United States Patent
Wagner et al.

[19]

[11] Patent Number: 5,989,250
[45] Date of Patent: Nov. 23, 1999

[54] METHOD AND APPARATUS FOR SPINAL FIXATION

[75] Inventors: Erik J. Wagner; Vincent J. Jannetty; Robert J. Jones, all of Austin, Tex.

[73] Assignee: Spinal Concepts, Inc., Austin, Tex.

[21] Appl. No.: 09/026,711

[22] Filed: Feb. 20, 1998

Related U.S. Application Data

[63] Continuation-in-part of application No. 08/942,325, Oct. 1, 1997, which is a continuation-in-part of application No. 08/740,123, Oct. 24, 1996.

[51] Int. Cl.⁶ ................................................. A61B 17/56
[52] U.S. Cl. ............................... 606/61; 606/60; 606/62; 606/72; 606/73
[58] Field of Search ................................. 606/61, 60, 62, 606/63, 64–73, 104, 105; 623/15, 16, 17, 18, 19

[56] References Cited

U.S. PATENT DOCUMENTS

| | | |
|---|---|---|
| 4,401,112 | 8/1983 | Rezaian . |
| 4,433,677 | 2/1984 | Ulrich et al. . |
| 4,492,226 | 1/1985 | Belykh et al. . |
| 4,501,269 | 2/1985 | Bagby . |
| 4,503,848 | 3/1985 | Caspar et al. . |

(List continued on next page.)

FOREIGN PATENT DOCUMENTS

| | | |
|---|---|---|
| 0578320A1 | 1/1994 | European Pat. Off. . |
| 0778007A1 | 6/1997 | European Pat. Off. . |
| 0836836 | 4/1998 | European Pat. Off. . |
| 2732887A1 | 10/1996 | France . |
| 2736535A1 | 1/1997 | France . |

OTHER PUBLICATIONS

Danek Group, Inc. Medical Division Publication entitled, "TSRH Spinal System—Ummatched versatility," 1992, pp. 1–4.

Danek Surgical Technique Manual entitled, "TSRH Spinal Implant System," Date Unknown, pp. 1–16.

Danek Surgical Technique Manual entitled, "TSRH Crosslink," Date Unknown, pp. 1–8.

Dickman Curtis A., et al., BNI Quarterly Publication entitled, "Techniques of Screw Fixation of the Cervical Spine," vol. 9, No. 4, Fall 1993, pp. 27–39.

Slone et al., RadioGraphics Publication entitled, "Spinal Fixation," vol. 13, No. 2, Mar. 1993, pp. 341–356.

(List continued on next page.)

*Primary Examiner*—Michael Buiz
*Assistant Examiner*—Lien Ngo
*Attorney, Agent, or Firm*—Conley, Rose & Tayon, PC

[57] ABSTRACT

A spinal fixation implant system for correction and fixation of the human spine to facilitate an anatomically correct fusion. The spinal fixation system may include a connector, a spinal rod, a spinal fixation component, a sleeve, and a fastener. The spinal fixation component preferably includes a fixation device such as a hook or screw for securing the spinal rod to vertebrae of the thoracic or lumbar spine. The spinal fixation component preferably includes a threaded end on its top that is adapted to receive the fastener. The fixation component may include a body having a tapered cavity for engaging the receiving end of the connector. Tightening of the fastener preferably downwardly translates the sleeve over the fixation component body to force the connector through the tapered cavity, which compresses the receiving end about the spinal rod to fixably connect the spinal rod and the spinal fixation component. In an alternate embodiment, assembly pliers may be used to move the connector into the tapered cavity. The fixation component may also include a rotatable fixation member. The spinal rod and connector may include a textured surface to inhibit movement of the connector with respect to the spinal rod. The fastener may be a clip configured to engage an indentation formed in the connector to secure the connector within the fixation component. The connector may include a tab which is configured to interact with a channel formed in the cavity to inhibit the removal of the connector from the cavity.

102 Claims, 18 Drawing Sheets

U.S. PATENT DOCUMENTS

| | | |
|---|---|---|
| 4,570,618 | 2/1986 | Wu . |
| 4,604,995 | 8/1986 | Stephens et al. . |
| 4,641,636 | 2/1987 | Cotrel . |
| 4,643,178 | 2/1987 | Nastari et al. . |
| 4,743,256 | 5/1988 | Brantigan . |
| 4,763,644 | 8/1988 | Webb . |
| 4,805,602 | 2/1989 | Puno et al. . |
| 4,834,757 | 5/1989 | Brantigan . |
| 4,878,915 | 11/1989 | Brantigan . |
| 4,887,596 | 12/1989 | Sherman . |
| 4,946,458 | 8/1990 | Herma et al. . |
| 4,950,269 | 8/1990 | Gaines, Jr. . |
| 4,961,740 | 10/1990 | Ray et al. . |
| 4,966,600 | 10/1990 | Songer et al. . |
| 4,987,892 | 1/1991 | Krag et al. . |
| 5,005,562 | 4/1991 | Cotrel . |
| 5,026,373 | 6/1991 | Ray et al. . |
| 5,047,029 | 9/1991 | Aebi et al. . |
| 5,055,104 | 10/1991 | Ray . |
| 5,074,864 | 12/1991 | Cozad et al. . |
| 5,102,412 | 4/1992 | Rogozinski . |
| 5,108,399 | 4/1992 | Eitenmuller et al. . |
| 5,108,446 | 4/1992 | Wagner et al. . |
| 5,116,340 | 5/1992 | Songer et al. . |
| 5,123,926 | 6/1992 | Pisharodi . |
| 5,127,912 | 7/1992 | Ray et al. . |
| 5,129,388 | 7/1992 | Vignaud et al. . |
| 5,129,904 | 7/1992 | Illi . |
| 5,147,359 | 9/1992 | Cozad et al. . |
| 5,154,718 | 10/1992 | Cozad et al. . |
| 5,171,278 | 12/1992 | Pisharodi . |
| 5,176,678 | 1/1993 | Tsou . |
| 5,176,680 | 1/1993 | Vignaud et al. . |
| 5,181,917 | 1/1993 | Rogozinski . |
| 5,192,321 | 3/1993 | Strokon . |
| 5,192,327 | 3/1993 | Brantigan et al. . |
| 5,201,734 | 4/1993 | Cozad et al. . |
| 5,242,445 | 9/1993 | Ashman . |
| 5,242,448 | 9/1993 | Pettine et al. . |
| 5,246,442 | 9/1993 | Ashman et al. . |
| 5,261,909 | 11/1993 | Sutterlin et al. . |
| 5,263,953 | 11/1993 | Bagby . |
| 5,281,222 | 1/1994 | Allard et al. . |
| 5,282,801 | 2/1994 | Sherman . |
| 5,290,312 | 3/1994 | Kojimoto et al. . |
| 5,290,494 | 3/1994 | Coombes et al. . |
| 5,303,718 | 4/1994 | Krajicek . |
| 5,304,179 | 4/1994 | Wagner . |
| 5,306,307 | 4/1994 | Senter et al. . |
| 5,306,309 | 4/1994 | Wagner et al. . |
| 5,312,405 | 5/1994 | Korotko et al. . |
| 5,312,410 | 5/1994 | Miller et al. . |
| 5,318,566 | 6/1994 | Miller . |
| 5,336,223 | 8/1994 | Rogers . |
| 5,336,240 | 8/1994 | Metzler et al. . |
| 5,344,422 | 9/1994 | Frigg . |
| 5,348,026 | 9/1994 | Davidson . |
| 5,357,983 | 10/1994 | Mathews . |
| 5,360,429 | 11/1994 | Jeanson et al. . |
| 5,360,431 | 11/1994 | Puno et al. . |
| 5,361,766 | 11/1994 | Nichols et al. . |
| 5,364,399 | 11/1994 | Lowery et al. . |
| 5,368,594 | 11/1994 | Martin et al. . |
| 5,380,325 | 1/1995 | Lahille et al. . |
| 5,385,583 | 1/1995 | Cotrel . |
| 5,390,683 | 2/1995 | Pisharodi . |
| 5,395,374 | 3/1995 | Miller et al. . |
| 5,397,364 | 3/1995 | Kozak et al. . |
| 5,403,315 | 4/1995 | Ashman . |
| 5,405,391 | 4/1995 | Hednerson et al. . |
| 5,415,658 | 5/1995 | Kilpela et al. . |
| 5,417,690 | 5/1995 | Sennett et al. . |
| 5,423,820 | 6/1995 | Miller et al. . |
| 5,423,825 | 6/1995 | Levine . |
| 5,425,772 | 6/1995 | Brantigan . |
| 5,466,237 | 11/1995 | Byrd, III et al. . |
| 5,474,555 | 12/1995 | Puno et al. . |
| 5,480,437 | 1/1996 | Draenert . |
| 5,484,437 | 1/1996 | Michelson . |
| 5,489,307 | 2/1996 | Kuslich et al. . |
| 5,489,308 | 2/1996 | Kuslich et al. . |
| 5,496,318 | 3/1996 | Howland et al. . |
| 5,505,732 | 4/1996 | Michelson . |
| 5,507,746 | 4/1996 | Lin . |
| 5,514,180 | 5/1996 | Heggeness et al. . |
| 5,520,690 | 5/1996 | Errico et al. . |
| 5,522,899 | 6/1996 | Michelson . |
| 5,527,341 | 6/1996 | Gogolewski et al. . |
| 5,531,746 | 7/1996 | Errico et al. . |
| 5,531,751 | 7/1996 | Schultheiss et al. . |
| 5,536,270 | 7/1996 | Songer et al. . |
| 5,536,271 | 7/1996 | Daly et al. . |
| 5,545,165 | 8/1996 | Biedermann et al. . |
| 5,549,608 | 8/1996 | Errico et al. . |
| 5,549,612 | 8/1996 | Yapp et al. . |
| 5,554,157 | 9/1996 | Errico et al. . |
| 5,563,124 | 10/1996 | Damien et al. . |
| 5,569,248 | 10/1996 | Mathews . |
| 5,569,253 | 10/1996 | Farris et al. . |
| 5,571,192 | 11/1996 | Schönhöffer . |
| 5,575,792 | 11/1996 | Errico et al. . |
| 5,578,033 | 11/1996 | Errico et al. . |
| 5,584,834 | 12/1996 | Errico et al. . |
| 5,586,984 | 12/1996 | Errico et al. . |
| 5,593,409 | 1/1997 | Michelson . |
| 5,601,553 | 2/1997 | Trebing et al. . |
| 5,601,556 | 2/1997 | Pisharodi . |
| 5,603,713 | 2/1997 | Aust et al. . |
| 5,607,424 | 3/1997 | Tropiano . |
| 5,607,425 | 3/1997 | Rogozinski . |
| 5,607,426 | 3/1997 | Ralph et al. . |
| 5,607,430 | 3/1997 | Bailey . |
| 5,609,592 | 3/1997 | Brumfield et al. . |
| 5,609,593 | 3/1997 | Errico et al. . |
| 5,609,594 | 3/1997 | Errico et al. . |
| 5,609,596 | 3/1997 | Pepper . |
| 5,609,635 | 3/1997 | Michelson . |
| 5,609,636 | 3/1997 | Kohrs et al. . |
| 5,611,800 | 3/1997 | Davis et al. . |
| 5,611,801 | 3/1997 | Songer . |
| 5,613,967 | 3/1997 | Engelhardt et al. . |
| 5,616,144 | 4/1997 | Yapp et al. . |
| 5,620,443 | 4/1997 | Gertzbein et al. . |
| 5,624,441 | 4/1997 | Sherman et al. . |
| 5,626,579 | 5/1997 | Muschler et al. . |
| 5,628,740 | 5/1997 | Mullane . |
| 5,628,756 | 5/1997 | Barker, Jr. et al. . |
| 5,630,816 | 5/1997 | Kambin . |
| 5,632,747 | 5/1997 | Scarborough et al. . |
| 5,634,925 | 6/1997 | Urbanski . |
| 5,643,260 | 7/1997 | Doherty . |
| 5,643,264 | 7/1997 | Sherman et al. . |
| 5,643,265 | 7/1997 | Errico et al. . |
| 5,645,084 | 7/1997 | McKay . |
| 5,645,544 | 7/1997 | Tai et al. . |
| 5,645,549 | 7/1997 | Boyd et al. . |
| 5,645,598 | 7/1997 | Brosnahan, III . |
| 5,647,873 | 7/1997 | Errico et al. . |
| 5,649,927 | 7/1997 | Kilpela et al. . |
| 5,651,283 | 7/1997 | Runciman et al. . |
| 5,651,789 | 7/1997 | Cotrel . |
| 5,653,708 | 8/1997 | Howland . |

| | | |
|---|---|---|
| 5,653,709 | 8/1997 | Frigg . |
| 5,653,763 | 8/1997 | Errico et al. . |
| 5,658,289 | 8/1997 | Boucher et al. . |
| 5,658,337 | 8/1997 | Kohrs et al. . |
| 5,658,516 | 8/1997 | Eppley et al. . |
| 5,662,653 | 9/1997 | Songer et al. . |
| 5,665,088 | 9/1997 | Gil et al. . |
| 5,665,112 | 9/1997 | Thal . |
| 5,665,122 | 9/1997 | Kambin . |
| 5,667,506 | 9/1997 | Sutterlin . |
| 5,667,507 | 9/1997 | Corin et al. . |
| 5,667,508 | 9/1997 | Errico et al. . |
| 5,668,288 | 9/1997 | Storey et al. . |
| 5,669,909 | 9/1997 | Zdeblick et al. . |
| 5,669,910 | 9/1997 | Korhonen et al. . |
| 5,669,911 | 9/1997 | Errico et al. . |
| 5,671,695 | 9/1997 | Schroeder . |
| 5,672,175 | 9/1997 | Martin . |
| 5,672,176 | 9/1997 | Biedermann et al. . |
| 5,674,222 | 10/1997 | Berger et al. . |
| 5,674,295 | 10/1997 | Ray et al. . |
| 5,674,296 | 10/1997 | Bryan et al. . |
| 5,676,665 | 10/1997 | Bryan . |
| 5,676,666 | 10/1997 | Oxland et al. . |
| 5,676,701 | 10/1997 | Yuan et al. . |
| 5,676,703 | 10/1997 | Gelbard . |
| 5,681,311 | 10/1997 | Foley et al. . |
| 5,681,312 | 10/1997 | Yuan et al. . |
| 5,683,391 | 11/1997 | Boyd . |
| 5,683,392 | 11/1997 | Richelsoph et al. . |
| 5,683,393 | 11/1997 | Ralph . |
| 5,683,394 | 11/1997 | Rinner . |
| 5,688,272 | 11/1997 | Montague et al. . |
| 5,688,273 | 11/1997 | Errico et al. . |
| 5,688,274 | 11/1997 | Errico et al. . |
| 5,688,279 | 11/1997 | McNulty et al. . |
| 5,688,280 | 11/1997 | Booth, Jr. et al. . |
| 5,690,629 | 11/1997 | Asher et al. . |
| 5,690,630 | 11/1997 | Errico et al. . |
| 5,690,631 | 11/1997 | Duncan et al. . |
| 5,690,632 | 11/1997 | Schwartz et al. . |
| 5,690,633 | 11/1997 | Taylor et al. . |
| 5,690,842 | 11/1997 | Panchison . |
| 5,693,046 | 12/1997 | Songer et al. . |
| 5,693,053 | 12/1997 | Estes . |
| 5,693,100 | 12/1997 | Pisharodi . |
| 5,697,929 | 12/1997 | Mellinger . |
| 5,697,977 | 12/1997 | Pisharodi . |
| 5,700,291 | 12/1997 | Kuslich et al. . |
| 5,700,292 | 12/1997 | Margulies . |
| 5,702,391 | 12/1997 | Lin . |
| 5,702,392 | 12/1997 | Wu et al. . |
| 5,702,393 | 12/1997 | Pfaifer . |
| 5,702,394 | 12/1997 | Henry et al. . |
| 5,702,395 | 12/1997 | Hopf . |
| 5,702,396 | 12/1997 | Hoenig et al. . |
| 5,702,399 | 12/1997 | Kilpela et al. . |
| 5,702,449 | 12/1997 | McKay . |
| 5,702,450 | 12/1997 | Bisserie . |
| 5,702,451 | 12/1997 | Biedermann et al. . |
| 5,702,452 | 12/1997 | Argenson et al. . |
| 5,702,453 | 12/1997 | Rabbe et al. . |
| 5,702,454 | 12/1997 | Baumgartner . |
| 5,702,455 | 12/1997 | Saggar . |
| 5,704,936 | 1/1998 | Mazel . |
| 5,704,937 | 1/1998 | Martin . |
| 5,707,372 | 1/1998 | Errico . |
| 5,707,395 | 1/1998 | Hopf . |
| 5,709,681 | 1/1998 | Pennig . |
| 5,709,682 | 1/1998 | Medoff . |
| 5,709,683 | 1/1998 | Bagby . |
| 5,709,684 | 1/1998 | Errico et al. . |
| 5,709,685 | 1/1998 | Dombrowski et al. . |
| 5,709,686 | 1/1998 | Talos et al. . |
| 5,713,841 | 2/1998 | Graham . |
| 5,713,898 | 2/1998 | Stucker et al. . |
| 5,713,899 | 2/1998 | Marnay et al. . |
| 5,713,900 | 2/1998 | Benzel et al. . |
| 5,713,903 | 2/1998 | Sander et al. . |
| 5,713,904 | 2/1998 | Errico et al. . |
| 5,716,355 | 2/1998 | Jackson . |
| 5,716,356 | 2/1998 | Biedermann et al. . |
| 5,716,357 | 2/1998 | Rogozinski . |
| 5,716,358 | 2/1998 | Ochoa . |
| 5,716,359 | 2/1998 | Ojima et al. . |
| 5,716,415 | 2/1998 | Steffee . |
| 5,716,416 | 2/1998 | Lin . |
| 5,720,746 | 2/1998 | Soubeiran . |
| 5,720,747 | 2/1998 | Burke . |
| 5,720,748 | 2/1998 | Kuslich et al. . |
| 5,720,751 | 2/1998 | Jackson . |
| 5,722,977 | 3/1998 | Wilhelmy . |
| 5,733,284 | 3/1998 | Martin . |

OTHER PUBLICATIONS

Synthes Spine Publication entitled, "The Universal Spinal System—Internal Fixation for the Spine," 1994, pp. 1–15.

AcroMed Publication entitled, "The ISOLA Spinal System—Versatility, simplicity and minimal profile in the surgical treatment of the spine," 1994, pp. 1–15.

AcroMed Corporation Publication entitled, "ISOLA® Transversa Rod Connectors: Principles and Techiques," Date Unknown, pp. i, ii, 1–8.

Danek Publication entitled, "AXIS—Fixation System," 1993, pp. 1–6.

Synthes Publication entitled, "Small Notched Titanium Reconstruction Plate System," 1996, pp. 1–6.

J. Neurosurg Publication entitled, "Posterior plates in the management of cervical instability: long–term results in 44 patients," vol. 81, 1994, pp. 341–349.

BNI Quarterly Publication entitled, "Lateral Mass Posterior Plating and Facet Fusion for Cervical Spine Instability," vol. 7, No. 2, 1991, pp. i, ii, 1–12.

Beadling, Lee, Orthopedics Today Publications entitled, "FDA Clears Spinal Cages for Interbody Lumbar Fusion," pp. 1–2.

MedPro Month Publication entitled, "Trends in Spine & Disk Surgery," vol. VI, No. 11–12, pp. 280–284.

Surgical Dynamics Ray Threaded Fusion Cage Device Surgical Technique Manual, pp. 1–10.

Surgical Dynamics Ray Threaded Fusion Cage, pp. 1–6.

AcroMed Publication entitled, "AcroMed Spinal Solutions for Cervical Pathologies," Jul. 1995, pp. 1–8.

Codman Publication entitled, "Sof'wire Cable System," 6 pp.

Huhn, Stephen L. et al., "Posterior Spinal Osteosynthesis for Cervical Fracture/Dislocation Using a Flexible Multistrand Cable System: Technical Note," Neurosurgery, vol. 29, No. 6, 1991, pp. 943–946.

Dickman, Curtis A. et al., "Wire Fixation for the Cervical Spine: Biomechanical Principles and Surgical Techniques," BNI Quarterly, vol. 9, No. 4, Fall 1993, pp. 2–16.

Publication by AcroMed entitled, "ACROMED Cable System by Songer," Sep. 1993, 4 pp.

M. Aebi, MD, et al., "Treatment of Cervical Spine Injuries with Anterior Plating: Indications, Techniques, and Results," vol. 16, No. 3S, Mar. 1991 Supplement, pp. S38–S45.

Foley, M.D. et al., "Aline Anterior Cervical Plating System," Smith & Nephew Richards, Inc. Orthopaedics Catalog Information, Sep. 1996, pp. 1–16.

Lowery, Gary L., M.D., Ph.D., Sofamor Danek Group, Inc. Publication entitled, "Orion Anterior Cervical Plate System: Surgical Technique," 1994, pp. 1–24.

Apfelbaum, R., M.D., Aesculap Scientific Information publication entitled, "Posterior Transarticular C1–2 Screw Fixation for Atlantoaxial Instability," 1993, pp. 1–15.

Danek Titanium Cable System publication by Danek Group, Inc., 1994, 6 pp.

Publication entitled, "Spinal Disorders", 4 pp.

O'Brien, John P., Ph.D., Orthopaedic Product News Article entitled, "Interbody Fusion of the Lumbar Spine," pp. 1–3.

Roy et al., "Variation of Young's Modulus and Hardness in Human Lumbar Vertebrae Measured by Nanoindentation", pp. 1–4.

Sofamor Danek publication entitled, "Atlas Cable System: Evolution of the Cable System for Spinal Applications," 1995, 2 pp.

AcroMed publication entitled, "AcroMed Songer Cable System: Ordering information for Implants and Instruments," Apr. 1996, 4 pp.

Songer, Matthew, M.D., "Acromed Cable System by Songer: Cervical Technique Manual," pp. 1–17.

Songer, Matthew N., M.D., "ACROMED Cable System by Songer: Technique Manual," 1993, pp. 1–20.

Oxland, Thomas R., Ph.D., et al., SpineTech Inc. Publication entitled, "Biomechnical Rationale—The BAK Interbody Fusion System: An Innovative Solution," pp. 1–16.

SpineTech, Inc. publication entitled, "Patient Information on Spinal Fusion Surgery and the BAK Interbody Fusion System," 10 pp.

SpineTech, Inc. publication entitled, "BAK/Cervical Interbody Fusion System," 1994, 2 pp.

SpineTech, Inc. publications entitled, "Instrumentation BAK Interbody Fusion System," "Biomechanics BAK Interbody Fusion System," and "Porosity BAK Interbody Fusion System," 1996, 12 pp.

SpineTech, Inc. publication entitled, "The BAK Interbody Fusion System," 1996, 4 pp.

Depuy Motech, Inc. publication entitled, "Moss Miami 3–Dimensional Spinal Instrumentation: Taking Spinal Instrumentation to a New Dimension," 1995, 8 pp.

Shufflebarger, Harry L., M.D., "Moss Miami Spinal Instrumentation System: Methods of Fixation of the Spondylopelvic Junction," *Lumbosacral and Spinopelvic Fixation*, 1996 by Raven Publishers, Philadelphia, pp. 381–393.

Shufflebarger, Harry L., M.D., Depuy Motech publications entitled, "Clinical Issue: Rod Rotation in Scoliosis Surgery," 5 pp.

AcroMed publication entitled, "Instruments," 3 pp.

SpineTech, Inc. publication entitled, "The Bone Harvester," 1996, 2 pp.

Wright Medical Technology Publications entitled, "Versalok Low Back Fixation System," 1996, pp. 1–4.

Danek Medical, Inc. Publication entitled, "TSRH Lumbar System," 1991, pp. 1–4.

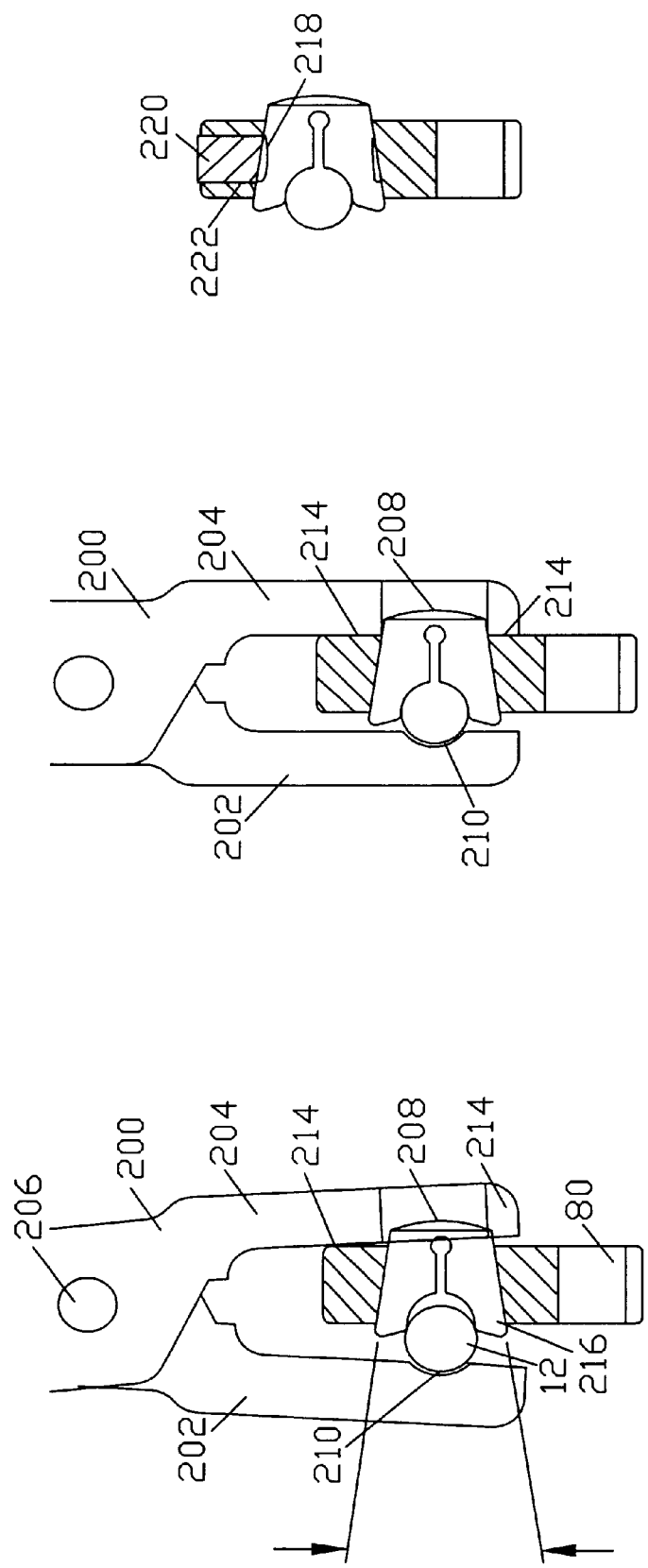

METHOD AND APPARATUS FOR SPINAL FIXATION

PRIOR APPLICATION

This application is a continuation-in-part of U.S. patent application Ser. No. 08/942,325 filed on Oct. 1, 1997 which is a continuation-in-part of U.S. patent application Ser. No. 08/740,123 filed on Oct. 24, 1996.

BACKGROUND OF THE INVENTION

1. Field of the Invention

The present invention generally relates to spinal fixation systems and the like. More particularly, an embodiment of the invention relates to a spinal implant system for correction, fixation, and stabilization of the human spine to allow the development of a solid spinal fusion.

2. Description of the Related Art

Spinal fixation, such as lumbar sacral fusion and the correction of spinal deformities such as scoliotic curves, is a well known and frequently used medical procedure. Pedicle, lateral, and oblique mounting devices may be used to secure corrective spinal instrumentation to a portion of the spine that has been selected to be fused by arthrodesis.

A spinal fixation system typically includes corrective spinal instrumentation that is attached to selected vertebrae of the spine by screws, hooks, and clamps. The corrective spinal instrumentation includes spinal rods or plates that are generally parallel to the patient's back. The corrective spinal instrumentation may also include transverse connecting rods that extend between neighboring spinal rods. Spinal fixation systems are used to correct problems in the lumbar and thoracic portions of the spine, and are often installed posterior to the spine on opposite sides of the spinous process and adjacent to the transverse process.

Various types of screws, hooks, and clamps have been used for attaching corrective spinal instrumentation to selected portions of the patient's spine. Examples of pedicle screws and other types of attachments are illustrated in U.S. Pat. Nos. 4,763,644; 4,805,602; 4,887,596; 4,950,269; and 5,129,388. Each of these patents is incorporated by reference as if fully set forth herein.

An eyebolt assembly of the TSRH® spinal system sold by Danek Medical Inc. is illustrated in FIG. 1. The eyebolt assembly 2 encircles spinal rod 4 such that assembly mass completely surrounds the spinal rod. The spinal rod must be inserted through the eyebolt, which rests within the yoke of spinal hook 8. The spinal hook attaches the spinal rod to a bony element of the spine. A nut 6 is threaded onto a post of the eyebolt assembly to fixably secure the rod within the yoke. The nut is tightened so that the assembly resists axial, torsional, and shear forces to inhibit motion of the spinal rod relative to the assembly in the directions indicated by the arrows in FIG. 1. Further details of the TSRH® spinal system are provided in the TSRH® Spinal Implant System Surgical Technique Manual and the TSRH® Crosslink Surgical Technique Manual. Both of these publications are available from Danek Medical Inc. and are incorporated by reference as if fully set forth herein.

Manual insertion of a spinal rod through the bores of a number of spaced-apart eyebolts within a surgical wound tends to be difficult. The bore axis of each eyebolt must be properly aligned along a common axis, which is difficult since the corrective procedure requires that the spinal rod initially be placed under stress to resist deforming forces of the spine. Therefore, the use of systems such as the TSRH® spinal system may require that a predetermined number of screws or hooks be pre-loaded onto the spinal rod in a particular order and spacing prior to the insertion of the spinal rod into the surgical wound. After insertion of the spinal system into the surgical wound, however, it is often necessary to add, delete, or reposition one or more hooks or screws. Before such modifications can be made, the spinal system typically must be removed from the surgical wound and at least partially disassembled.

To overcome such problems, some spinal fixation systems include "open back" hooks or screws to allow a spinal rod to be dropped into the open back of the hook or screw and secured within the open back by a separate component and a set screw. Such a system is illustrated in U.S. Pat. No. 5,102,412 to Rogozinski, which is incorporated by reference as if fully set forth herein. Such systems tend to be susceptible to fatigue stress failure and require assembly within the surgical wound. In addition, adding a hook or screw to the construct tends to require that the spinal rod first be repositioned. A further disadvantage of this approach is that component mass completely surrounds the spinal rod, resulting in an increase in the profile width of the device and greater impingement of the device upon the fusion mass. A low profile width is generally desired to minimize sinus formation and soft tissue irritation from hardware prominence.

U.S. Pat. No. 5,242,445 to Ashman relates to a "split eyebolt" assembly for adding eyebolts to an assembled spinal fixation construction. Attaching the split eyebolt to a spinal rod requires a special crimping tool to crimp the split eyebolt over the rod. The crimping tool tends to be difficult to operate within the surgical wound. Furthermore, the threads of the opposing sides of the split eyebolt are often misaligned after crimping, making it difficult or impossible to thread a nut onto the split eyebolt. The split eyebolt also completely encircles the spinal rod thereby increasing the impingement of the construct upon the fusion mass.

It is therefore desirable that an improved spinal fixation system be derived that facilitates assembly and surgical implantation by allowing the spinal rod to be positioned within the surgical wound (a) after the fixation components (e.g., screws, hooks) have been implanted, (b) without modifying the fixation components, and (c) whereby fixation components may be subsequently added, deleted, and/or repositioned without disassembling the system.

SUMMARY OF THE INVENTION

In accordance with the present invention, a spinal fixation system is provided that largely eliminates or reduces the aforementioned disadvantages of conventional spinal fixation constructions. An embodiment of the invention relates to an implant system for fixation of the human spine that includes a spinal rod, a fixation component, a connector, and a fastener.

The connector may be used to connect the spinal rod to the fixation component and preferably includes a receiving end and a fastening end. The receiving end may contain a first arm and a second arm that together form a substantially U-shaped borehole into which the spinal rod may be axially positioned. The receiving end preferably surrounds only part of the spinal rod such that the unsurrounded portion of the spinal rod is exposed from the borehole. The exposed portion of the spinal rod may extend out of an open end of the U-shaped borehole. The spinal rod may be circular and preferably includes a cross-section having a circumferential portion. The receiving end of the connector preferably surrounds and engages greater than about radians and less than about 2π radians of the circumferential portion.

The receiving end of the connector preferably acts as a "pinch clamp" by exerting a clamping force on opposing sides of the spinal rod to secure the spinal rod within the borehole. The connector preferably contains a slot between the receiving end and the fastening end that enables the first arm and the second arm to be deflected relative to one another. The deflection of the arms allows the distance between a tip of the first arm and a tip of the second arm to be changed so that the spinal rod may be inserted through an open end of the U-shaped borehole that is defined between the tips of the arms.

The fixation component preferably includes a fixation device such as a bone screw or hook for engaging vertebrae of the thoracic or lumbar spine. The fixation component also preferably includes a body containing a cavity with an inner surface. The cavity is preferably sized to receive a portion of the connector. The connector is preferably partially disposed within the cavity such that at least a portion of the fastening end extends from the cavity, whereby the inner surface of the cavity engages an outer surface of the receiving end. The cavity of the body is preferably a tapered cavity that narrows in a direction from a first end of the cavity to a second end of the cavity. The tapered cavity preferably surrounds a portion of the receiving end and imparts a compressive force against the receiving end to secure the spinal rod within the borehole.

The fastener preferably engages both the body and the portion of the fastening end that extends from the cavity. The fastener may secure the connector and the fixation component together. The fastener is preferably a nut adapted to be threaded upon the fastening end. The fastener may be selectively tightened to allow an engagement between the connector and the spinal rod that may be overcome by the application of a distraction force to the connector. Rotation of the nut in a tightening direction about the fastening end preferably draws a portion of the receiving end through the tapered cavity, causing the inner surface of the cavity to compress the arms of the receiving end. In turn, the arms may exert a compressive force against the spinal rod to clamp it within the borehole. The magnitude of the compressive force against the spinal rod preferably varies as a function of the degree to which the nut is tightened. The open end of the U-shaped borehole preferably has a width that can be adjusted by tightening the fastener.

The fixation component may include a spacer located between the fastener and the spinal rod for laterally offsetting the fixation device a selected lateral distance from the spinal rod. The spacer may include a surface having a plurality of radially-spaced teeth. The fixation component may comprise a plurality of radially-spaced protrusions adapted to fit adjacent to the teeth on the surface of the spacer. The tightening of the nut preferably causes the spacer and the fixation component to become pressed together such that a complementary engagement between the teeth of the spacer and the protrusions of the fixation device is formed to inhibit rotation of the fixation device about the spacer.

The body may include a U-shaped yoke formed between a top section and a bottom section that each have an edge adjacent to the yoke. The tapered cavity preferably is formed between the top section and the bottom section and extends in a perpendicular direction relative to the U-shaped yoke. The fixation component is preferably adapted to pivot about the spinal rod in a substantially vertical plane. The edges of the top and bottom sections preferably contact the spinal rod during the pivoting of the fixation component to define the range of pivotal motion of the fixation component about the spinal rod. The edges are preferably curved in a direction away from the spinal rod to increase the range of pivotal motion of the fixation component.

The fixation component may include a transverse connector to maintain a fixed distance between the spinal rod and a neighboring spinal rod. The transverse connector may include a reduced section that has a width less than that of the body, allowing the reduced section to be more easily bent. The reduced section may be bent to shorten the lateral distance between the spinal rod and an adjacent spinal rod. The transverse connector may contain a beveled section between the body and the reduced section.

In an embodiment, the connector includes a receiving end forming a substantially U-shaped borehole and a capped end opposite the receiving end. The connector may be forced into the cavity of a fixation component body with an instrument such as a pair of assembly pliers. Of The instrument preferably includes a first elongated member and a second elongated member. The elongated members may be moved relative to one another to exert a compressive force against the connector and the fixation component to move the connector within the cavity of the fixation component body. The first elongated member preferably includes a curvate indention for engaging the spinal rod. The second elongated member preferably includes a borehole for receiving an end of the connector.

In an embodiment, the fixation component includes a fastening end. The fastening end preferably is adapted to receive a fastener (e.g., threaded nut). Downward translation of the fastener preferably moves a sleeve downwardly over the body of the fixation component. The sleeve preferably contains a substantially U-shaped opening having a angled locking surface for engaging the spinal rod. During assembly, the fastener is preferably tightened to move the sleeve downwardly, thereby imparting a force on the spinal rod that causes the connector to move through the tapered cavity.

In an embodiment the fixation component may include a pivotable fixation device. The fixation device is preferably adapted to pivot about the body of the fixation component along the longitudinal axis of the body. The body of the fixation component may be adapted to inhibit the lateral motion of the fixation device. The body of the fixation component may be adapted to engage a portion of the connector.

In an embodiment the connector may include an opening adapted to completely surround the circumferential portion of the spinal rod. The connector may include a slot running through the center of the connector, communicating with the opening. The slot may be adapted to allow the circumference of the opening to vary. Insertion of a spinal rod preferably causes the slot to widen such that the circumference of the opening increases. The connector may be placed within the fixation component such that the slot is narrowed to secure a spinal rod to the connector.

In an embodiment, movement of the connector with respect to the spinal rod may be further inhibited by texturing either the surface of the spinal rod or the inner surface of the connector (i.e., the surface of the connector that contacts the spinal rod). Preferably, both surfaces are textured to inhibit movement of the connector with respect to the spinal rod. A number of textured surfaces may be used to increase the coefficient of friction between the inner surface of the connector and the spinal rod. In general, any process which transforms a relatively smooth surface into a roughened surface having an increased coefficient of friction may be used. Methods for forming a roughed surface include, but are not limited to: sanding, forming grooves within a surface, ball peening processes, electric discharge processes, and embedding of hard particles within a surface. These processes may also be used to increase the coefficient of friction between the fixation component and the connector.

In an embodiment, a connector is preferably coupled to a fixation component. The fixation component preferably includes a body and a fixation device. The body preferably includes an upper cavity configured to receive a connector. The fixation component preferably includes a lower cavity to hold a fixation device. The fixation device preferably includes a head. An opening preferably extends through the central portion of the head. A substantially cylindrical pin is preferably positionable within the head and the body such that the fixation device may be rotated about pin along the longitudinal axis of the body.

The head may include two substantially flat portions. The flat portions are formed on the head proximate the wall which divides the lower cavity from the upper cavity. The flat portions preferably interact with the wall to restrict rotation of the fixation device.

In an embodiment, a connector is coupled to a fixation component. The fixation component preferably includes a body and a fixation device. The body preferably includes an upper cavity adapted to receive connector. The fixation device is preferably rotatable as previously described. The connector preferably includes a fastening end and a receiving end opposite the fastening end. The fastening end is preferably adapted to engage a fastener. The fastener is preferably a nut. The receiving end preferably includes a pair of arms that together form a U-shaped borehole.

In an embodiment where the fastener is a nut, tightening of the fastener is accomplished by rotating the fastener in a tightening direction. As the fastener is tightened, the arms are preferably deflected toward one another such that the slot is narrowed and the arms of the receiving end exert a compressive force against the spinal rod disposed within the borehole.

In an embodiment, fixation component preferably includes a tapered cavity for receiving connector as in the above described embodiments. The fixation system preferably includes a clip that is configured to fit about a portion of connector. The clip is preferably configured to inhibit removal of the connector from the tapered cavity after a locking taper engagement is formed. The fixation component preferably includes a body and a fixation device coupled to the body. The body preferably includes the tapered cavity. The fixation device may be a monoaxial device (i.e., a non-rotatable device) or a polyaxial device (i.e., rotatable) as described in previous embodiments. The connector preferably includes a fastening end and a receiving end opposite the fastening end. The receiving end preferably includes a pair of arms that together form a U-shaped borehole. Spinal rod is preferably positionable within the borehole.

The fastening end includes two indentations, formed on opposite sides of the fastening end. The indention is preferably formed such that the distance between sidewalls is variable. Preferably, the distance between sidewalls proximate the first end is substantially greater than the distance between the sidewalls proximate the second end. In this manner the indentation is substantially tapered.

The indentation is configured to couple with clip to inhibit movement of the connector through the fixation component. The clip preferably includes two arms which together define a substantially U-shaped opening. Each of the arms preferably includes an upper portion and a lower portion. The lower portions of each of the arms are separated from each other by a distance equal to or greater than the diameter of the connector.

The clip is preferably coupled to the connector after a locking taper engagement has been formed between the connector and fixation component. The formation of the locking taper engagement preferably leaves a portion of the fastening end extending from the fixation component. The indentation preferably is exposed when a locking taper engagement is formed. The clip is positioned such that the upper portion of the clip engages a portion of the indentation.

The clip is preferably tapered in a manner complimentary to the tapering of the indentation. As the clip is inserted through indentation, an interference fit between the arms of the clip and the sidewalls of the indentation is preferably formed. As the clip is further inserted into the indentation the interference fit preferably becomes stronger. In this manner the clip may be secured within the indentation.

In an embodiment, fixation component preferably includes a tapered cavity for receiving connector as in the above described embodiments. The connector preferably includes a tab configured to inhibit removal of the connector from the tapered cavity after a locking taper engagement is formed.

The tab is preferably formed proximate the top of the receiving end. The tab preferably extends out from the outer surface of the connector. The cavity preferably contains a channel for receiving tab. The channel preferably has a width that is slightly larger than a width of the tab. When a locking taper engagement is formed the connector is positioned within the cavity such that the tab is preferably positioned within the channel. Preferably, the tab is formed on the connector such that the tap resides within a central portion of the channel when the connector is secured within the cavity. A bottom edge of the channel preferably prevents further movement of the connector toward a first side of the fixation component.

An advantage of the present invention relates to a fixation component that may be added to or deleted from a spinal fixation construct in a surgical wound without disassembling the construct.

Another advantage of the present invention relates to a spinal fixation system requiring minimal assembly within the surgical wound.

Yet another advantage of the present invention relates to a spinal fixation system having a relatively narrow profile width to reduce impingement upon the fusion mass.

BRIEF DESCRIPTION OF THE DRAWINGS

Further advantages of the present invention will become apparent to those skilled in the art with the benefit of the following detailed description of the preferred embodiments and upon reference to the accompanying drawings in which:

FIG. 12 depicts a side view partially in section of a spinal fixation system prior to assembly;

FIG. 13 depicts a side view partially in section of a spinal fixation system assembled with an instrument;

FIG. 14 depicts a side view partially in section of a spinal fixation system that includes a set screw engaging a connector;

Figure 1:
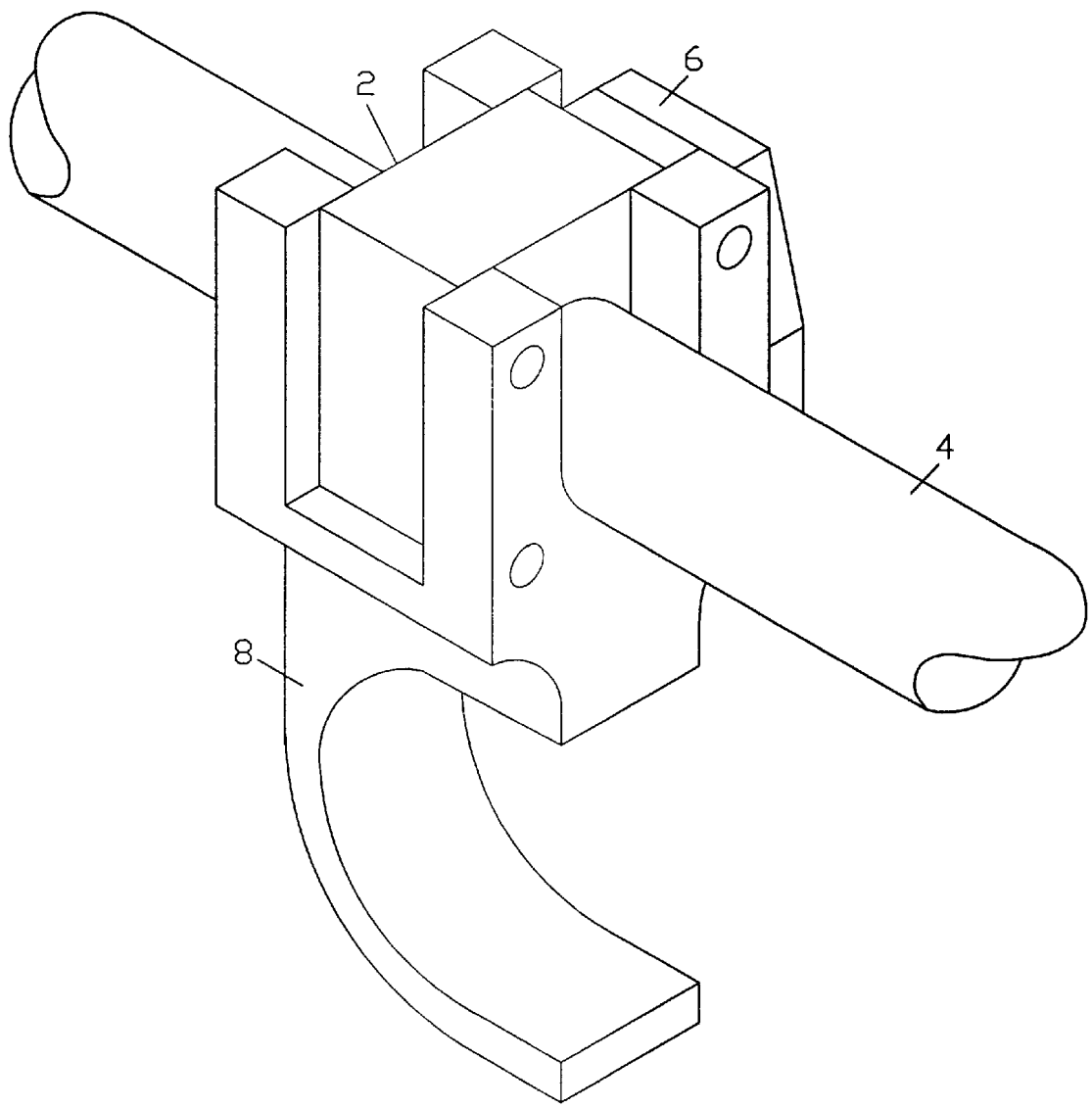
FIG. 1 depicts a TSRH® spinal system eyebolt assembly.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Figure 2:
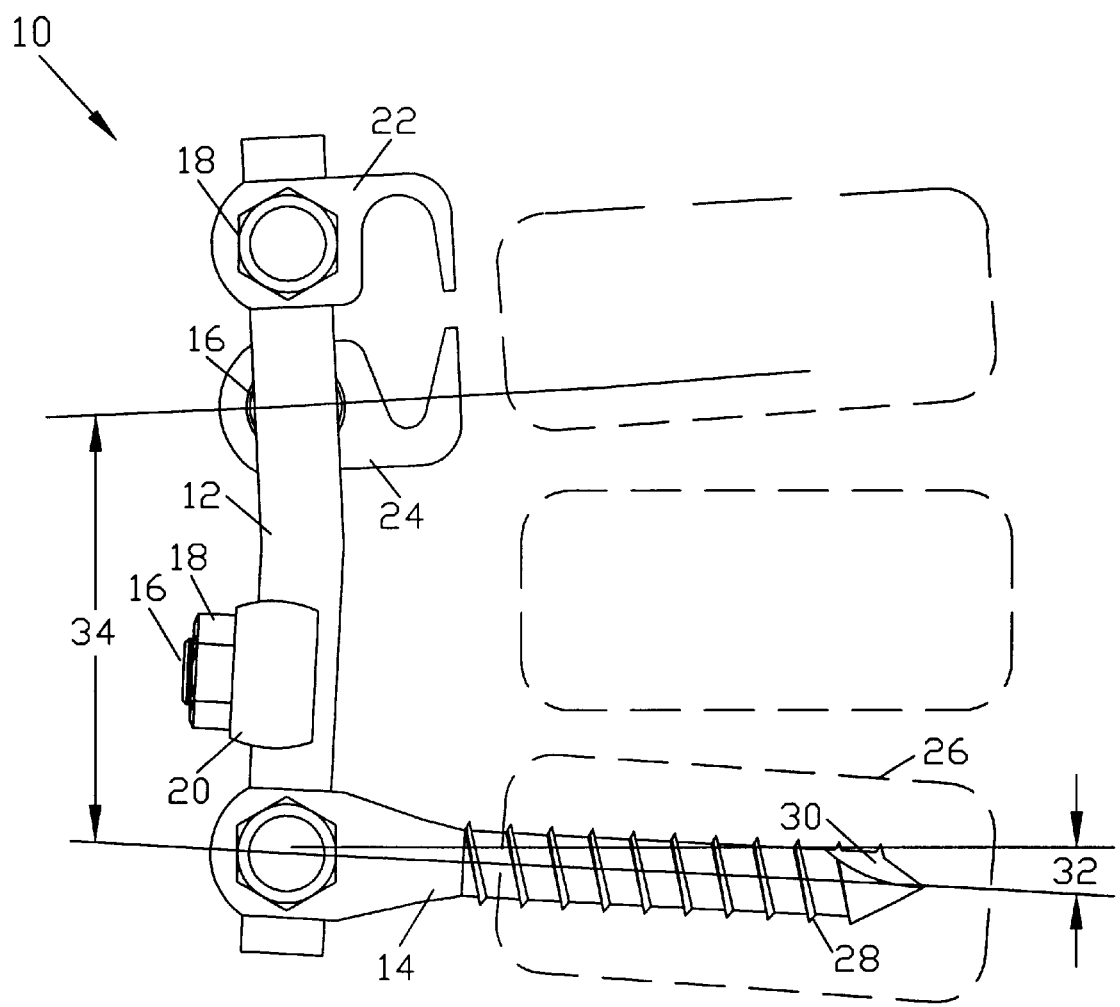
FIG. 2 depicts a side view of an embodiment of a spinal fixation system connected to a vertebra.

FIG. 2 depicts a spinal fixation system 10 constructed according to teachings of the present invention. In an embodiment of the invention, spinal fixation system 10 includes a spinal rod 12 generally aligned parallel with a portion of the spine. Connector 16 secures spinal fixation components to the spinal rod via fastener 18. The fixation components may include various fixation devices including bone screw 14, transverse connector 20, and spinal hooks 22 and 24.

Spinal rod 12 is preferably constructed of stainless steel or another relatively rigid material. The spinal rod preferably has a substantially circular cross-section (although other cross-sectional geometries may be employed) and a diameter between about ⅛ of an inch and about ¼ of an inch. The spinal rod may have a shot-peened surface to increase its resistance to fatigue failure. The spinal rod may impart forces against the spine to maintain a portion of the spine in a fixed position to correct a spinal deformity or injury. The spinal rod may be contoured to a selected shape prior to or after surgical implantation.

Bone screw 14 is preferably inserted within the main body of a vertebra 26 and may contain threads 28 to create a fixable engagement with the vertebra. Alternatively, the bone screw may have a substantially smooth shank containing no threading. The stress imparted to spinal fixation systems resulting from a spinal deformity may cause fatigue failure of a threaded bone screw if a solid spinal fusion does not develop after a period of time. Threaded screws having relatively long shanks tend to fail at a location adjacent to the screw head. A substantially smooth, unthreaded shank tends to remove the stress concentration on the screw shank from a location adjacent to the screw head where failure of the screw often occurs. The bone screw may also include a tap relief 30 to facilitate its insertion into vertebra 26. The angle of the bone screw relative to the spinal rod is preferably adjustable. The bone screw may be angled to correct the angle 32 of a vertebra relative to other vertebrae in the spine. The angle between the bone screw and spinal rod is preferably fixable by tightening fastener 18. Furthermore, the height of the vertebra 26 may be adjusted by applying a distraction force in the directions indicated by arrow 34 between a pair of fixation devices such as bone screw 14 and spinal hook 24 prior to tightening fasteners 18. The distraction force may be applied with the use of a tool in a manner well known to those skilled in the art.

The spinal hooks 22 and 24 may be any of a number of types of hooks well known to those skilled in the art including large laminar, small laminar, thoracic laminar, and pedicle hooks. Each spinal hook may be positioned in the caudal direction (illustrated by hook 24 in FIG. 2) or in the cranial direction (illustrated by hook 22 in FIG. 2). Spinal hooks may be positioned on opposing sides of the spinal rod as shown in FIG. 2.

Figure 3:
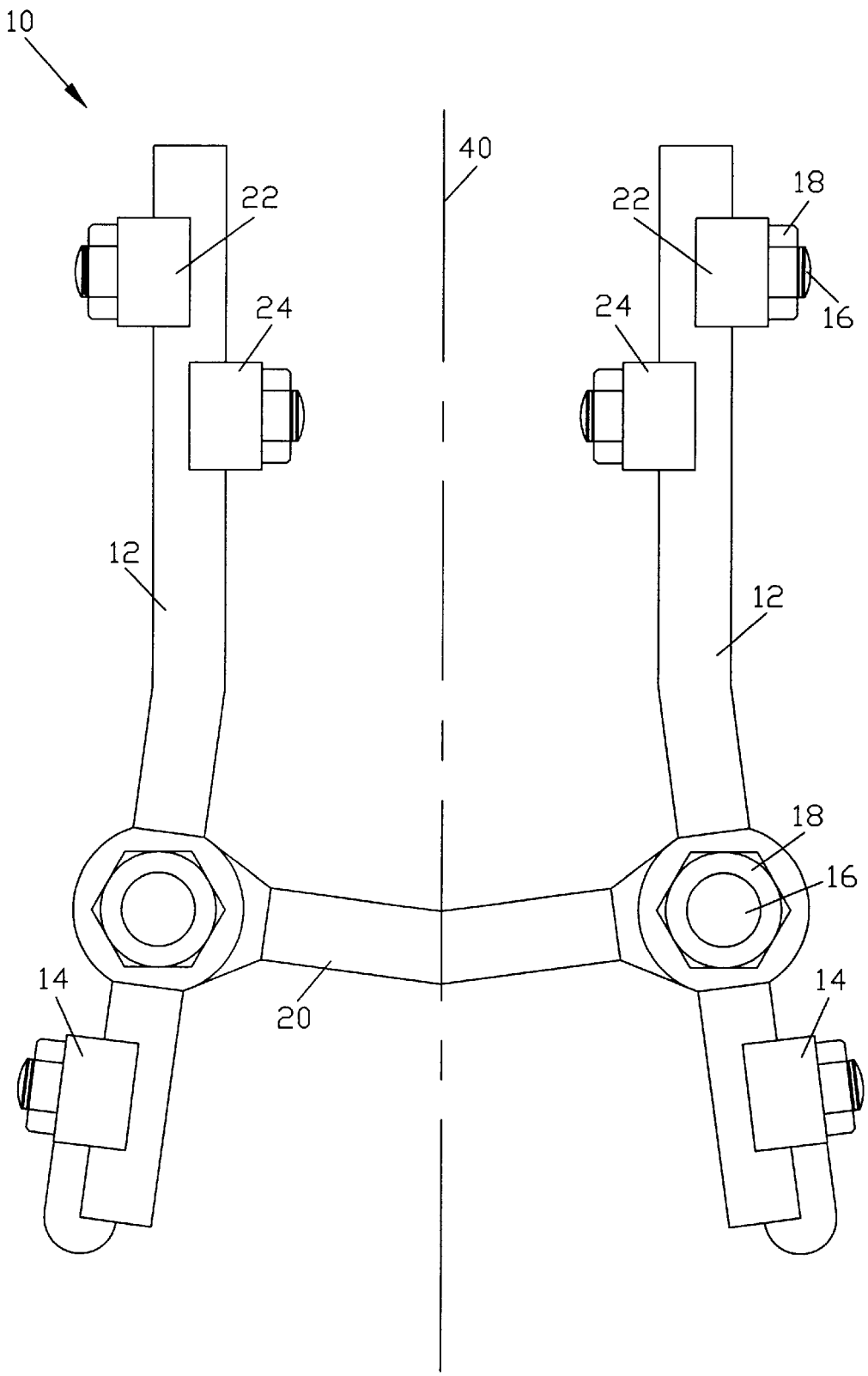
FIG. 3 depicts a top view of the spinal fixation system of FIG. 1.

FIG. 3 depicts a top view of an embodiment of spinal fixation system 10 that includes a pair of spinal rods 12 in spaced relation on each side of the vertical axis 40 of the spine. Spinal hooks 22 and 24 are preferably positioned for attachment to bony elements of the posterior human spine. One or more transverse connectors 20 may be used to rigidly link the rods to improve the strength of the assembly. Each of the fixation components may be attached to the spinal rod using a fastener 18 that engages connector 16 and the fixation component.

Transverse connector 20 may connect neighboring rods to increase the rigidity of the construct and to prevent the movement of the rods relative to one another. The transverse connector may be attached to the spinal rod using crosslinking plates that are well known to those skilled in the art and described in the TSRH® Crosslink Surgical Technique Manual, which is incorporated by reference herein. It is preferred that neighboring rods be connected by two transverse connectors that may be aligned parallel and in spaced relation from one another. If the spinal rod is bent, transverse connector 20 is preferably attached to the spinal rod at a location other than the "peak" of the curved section of the rod so that additional stress is not placed at that location.

Figure 4:
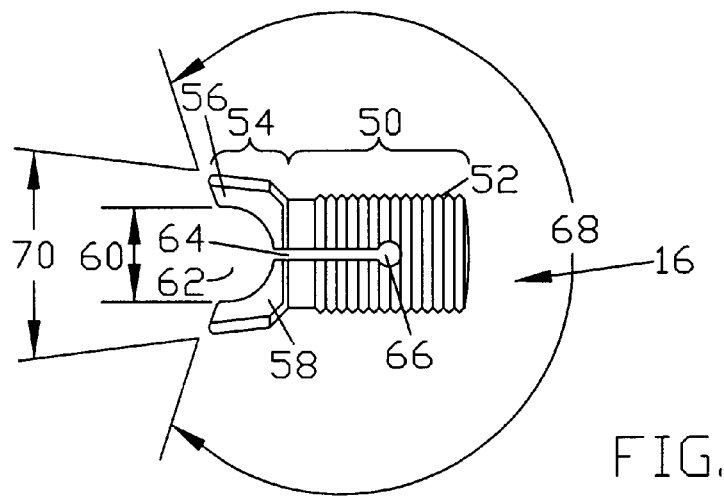
FIG. 4 depicts a side view of a tapered connector constructed in accordance with the present invention.

An embodiment of connector 16 is illustrated in FIG. 4. The connector preferably includes a fastening end 50 and a receiving end 54 opposite the fastening end. The fastening end may be a threaded end containing male machine threads 52 that are adapted to engage a fastener. The fastener is preferably a nut. The receiving end preferably includes a first arm 56 and a second arm 58 that together form a U-shaped borehole 62. The first arm has a tip 72 and the second arm has a tip 74 (each labeled in FIG. 5), and an opening 60 or open end is preferably defined by the tips of the first and second arm. A slot 64 preferably extends between the receiving end and the fastening end. The slot may extend from borehole 62 proximate the receiving end to a location proximate the fastening end. The slot may terminate in an enlarged opening 66 within the receiving end. The borehole is preferably adapted to receive a spinal rod 12 such that the first and second arms of the receiving end surround more than about half of a circumferential portion of the spinal rod.

The connector preferably does not completely surround the perimeter of the spinal rod. The unsurrounded portion of the spinal rod is preferably exposed from the open end 60 of the U-shaped borehole and may extend from the borehole through the open end. It is preferred that component mass be placed around only slightly greater than one-half of the circumference of the spinal rod to minimize the profile width of the construct. In this manner, the impingement of the construct upon the fusion mass is lessened, thereby reducing irritation of the surrounding tissue and facilitating the development of a correct spinal fusion in a minimal amount of time. Conventional assemblies tend to completely surround the spinal rod with component mass, causing a relatively greater impingement upon the fusion mass, which may interfere with fusion development.

The angle 68 in FIG. 4 is defined by the circumferential portion of a spinal rod that is surrounded by the first arm, second arm, and the end of slot 64. The angle 68 is preferably less than about $2\pi$ radians (e.g., 360° around the cross-section of the spinal rod) and greater than about $\pi$ radians (e.g., 180° around the cross-section of the spinal rod). It is preferred that more than about half of the circumferential portion the spinal rod be surrounded by a portion of the receiving end (e.g., first arm, second arm, end of slot 64) to allow the spinal rod to be adequately secured within the borehole. If less than half of the circumferential portion of the spinal rod were surrounded by the receiving end, forces resulting from spinal deformations might tend to pull the spinal rod from within borehole 62. First arm 58 and second arm 68 preferably engage the surface of greater than about half of the circumferential portion of the spinal rod.

The first arm and the second arm preferably each have an outside surface that is slightly tapered such that the distance between the outside surfaces of the arms narrows in a direction from tips 72 and 74 to the fastening end 50. The taper of the outside surfaces of the arms preferably defines a locking angle 70. Locking angle 70 is preferably a conical angle, although it may be formed within a substantially flat wedge instead. Locking angle 70 is preferably less than about 30°, more preferably less than about 25°, and more preferably still between about 1° and about 20°.

Figure 5:
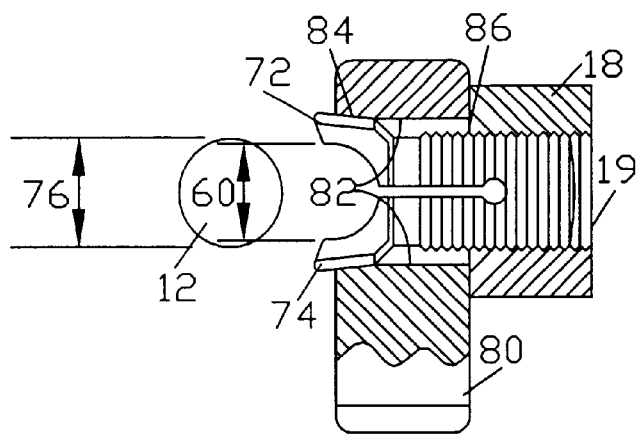
FIG. 5 depicts a side view of a tapered connector prior to assembly with a fixation component body and a spinal rod.
Figure 6:
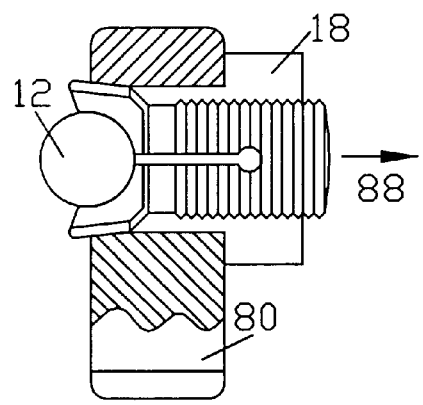
FIG. 6 depicts a side view of a tapered connector assembled with a spinal fixation component and a spinal rod.

FIGS. 5 and 6 illustrate the insertion of spinal rod 12 within borehole 62 in an embodiment of the invention. The spinal rod is preferably axially positioned within the borehole by passing the spinal rod through opening 60. Slot 64 preferably enables deflection of the first arm and the second arm relative to one another to allow the width of opening 60 to be altered. In the absence of an external force of a selected magnitude against the first or second arms, the width of opening 60 is preferably less than the outside diameter 76 of the spinal rod. Receiving end 54 is preferably adapted to form a "snap-fit" engagement with the spinal rod that may be realized by forcing the spinal rod into the inner surfaces of tips 72 and 74 of the first and second arms, respectively. The force against the inner surfaces of the tips 72 and 74 preferably causes the arms to slightly deflect in opposite directions, resulting in a slight widening of at least a portion of the slot. In this manner, the width of opening 60 may be increased by an amount sufficient to allow the insertion of the spinal rod through opening 60 and into the borehole. Once the spinal rod is fully inserted within the borehole (as shown in FIG. 6), the arms preferably move back toward one another, causing the slot to narrow to its initial, unstressed width. If the diameter of the spinal rod is slightly greater than that of the borehole, the arms may remain slightly deflected and the slot may remain slightly widened after the spinal rod is snapped into the borehole. It is generally preferred that the diameter of the spinal rod and the diameter of the borehole be equal.

In an embodiment of the invention, connector 16 connects the spinal rod to a fixation component that engages a portion of the spine. The fixation component preferably includes a fixation device such as a bone screw, hook, transverse connector, or similar device. The fixation component preferably includes a body 80 having a tapered cavity into which connector 16 may be inserted. The tapered cavity preferably tapers in a direction that is substantially perpendicular to the longitudinal axis of the fixation component. The tapered cavity preferably has a first end 84, a second end 86, and an inside surface 82. The inside surface 82 is preferably tapered at an angle that corresponds to locking angle 70. The tapered cavity preferably narrows in a direction from first end 84 to second end 86. The tapered cavity is preferably sized so that fastening end 50 and a portion of receiving end 54 may be inserted within the tapered cavity through an aperture proximate the first end. The outer width of the receiving end proximate tips 72 and 74 is preferably slightly greater than the width of the aperture proximate the first end, thereby inhibiting the complete insertion of the receiving end into the tapered cavity.

Fastener 18 may be a hex nut and preferably contains female threading 19, which is sized to fit the male machine threads of the fastening end 50. The nut preferably engages fastening end 50 and body 80 whereby rotating the fastener in a tightening direction creates a tensile force in the connector in direction 88. Tightening of the fastener preferably moves the connector within the tapered cavity in a direction from first end 84 to second end 86, thereby creating an interference fit between the arms of the receiving end and inside surface 82. As the fastener is tightened, the arms are preferably deflected toward one another such that the slot is narrowed and the arms of the receiving end exert a compressive force against the spinal rod disposed within the borehole.

The magnitude of the compressive force exerted by the receiving end on the spinal rod is preferably variable as a function of the degree to which the fastener is tightened. The fastener may be selectively tightened so that the connector is "loosely" engaged to the spinal rod. The "loose" engagement preferably fixes the position of the connector on the rod in the absence of a selected force against the connector, while allowing the connector to slide over the surface of the rod upon receiving a distraction force. For instance, the fastener may be partially tightened to loosely attach a connector and fixation device onto the rod at a selected location. A distraction force may be applied to the connector to move the connector to a selected location on the rod, and the fastener may then be fully tightened to maintain the connector at the selected location.

The arms 56 and 58 preferably exert a clamping force onto "opposite sides" of the rod (i.e., sections of the outer surface of the spinal rod that are separated by about 180°). The engagement between the arms 56 and 58 and the "opposite sides" of the spinal rod preferably "centers" the rod within the borehole as shown in FIG. 6 so that substantially no gaps exist between the inner surface of the arms and the spinal rod. The rod may be constrained on opposing sides in this manner to provide further resistance to forces that might otherwise result in axial movement of the rod. When the arms 56 and 58 are deflected to engage the spinal rod, the receiving end preferably forms a "locking taper" engagement with the spinal rod. A "locking taper" engagement is taken to mean a largely irreversible deflection of the receiving end. That is, if the fastener becomes loose after the receiving end has been compressed about the spinal rod, the clamping force exerted by the receiving end will be maintained to fixably hold the spinal rod within the borehole.

Figure 7:
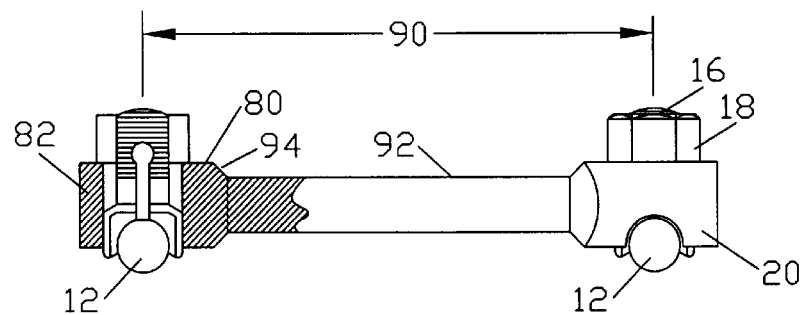
FIG. 7 depicts a side view of a transverse connector disposed between a pair of spinal rods in accordance with the present invention.

In an embodiment of the invention depicted in FIG. 7, a transverse connector 20 is disposed between a pair of spinal rods in spaced relation to secure the rods at a fixed distance 90. The spinal rods are fixed within the borehole of a connector in the manner depicted in FIGS. 5 and 6 and described above. The transverse connector may include a beveled surface between body 80 and a reduced section 92. Reduced section 92 preferably has a smaller width or diameter than body 80 to allow the reduced section to be bent more easily. Slight variations in distance 39 may be achieved by bending transverse connector 20 proximate reduced section 92. The bending of the transverse connector may be accomplished using a rod bender and a method well known to those skilled in the art. Alternately, the transverse connector may have a substantially constant width or diameter such that the width of section 92 and the width of body 80 are approximately equal.

Figure 8:
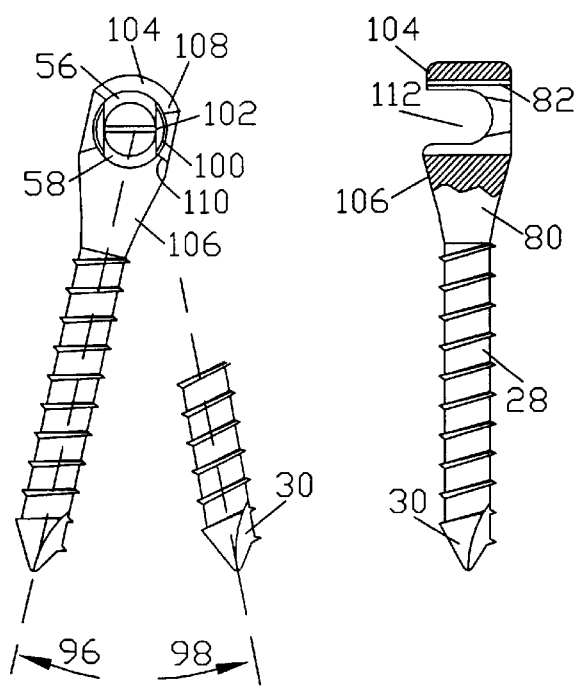
FIG. 8 depicts a front view and side view partially in section of a bone screw constructed according to teachings of the present invention.

The fixation component may include a bone screw that is used to correct the angle 32 between vertebrae. It is preferred that the bone screw be adapted to pivot about the spinal rod to form an oblique angle between the longitudinal axis of the spinal rod and the shank of the bone screw. The bone screw preferably can be pivoted in either direction 96 or direction 98 such that an oblique angle between about 90° and about 60° is formed between the shank and the longitudinal axis of the spinal rod. Other fixation devices (e.g., hooks) may be pivoted with respect the spinal rod in the same manner. As illustrated in FIG. 8, the tapered cavity may contain an engaging side 100 adapted to contact flat 102 of connector 16 to limit the pivoting of a fixation device (e.g., bone screw) about the spinal rod within a selected range, thereby preventing a gross misalignment that might complicate the assembly of the construct during a surgical procedure.

Body 80 preferably includes a top section 104 and a bottom section 106 that together form a U-shaped yoke 112 that is substantially perpendicular to inside surface 82 of the tapered cavity. The fixation component may pivot about the spinal rod. The edges of top section 104 and/or bottom section 106 may contact the spinal rod to prevent the pivoting of the fixation component about the spinal rod beyond a selected degree. Top section 104 preferably contains a curved edge 108, and bottom section 106 preferably contains a curved edge 110. Curved edges 108 and 110 preferably increase the degree that the fixation component can pivot and allow a fixation device (e.g., bone screw 14) to form an angle within a selected range that is perpendicular with or oblique to the spinal rod.

In an embodiment of the invention, body 80 is laterally offset from the spinal rod. Body 80 may contain a spacer 114 that extends laterally to offset a fixation component from the spinal rod. Offsetting a fixation component from the spinal rod may reduce the degree that the spinal rod must be contoured for proper positioning of bone screws (e.g., pedicle screws) in regions of the spine such as the lower lumbar region. The offset between the fixation component and the spinal rod may be equal to the width of the spacer. The offset is preferably less than about 15 mm, more preferably less than about 10 mm, and more preferably still between about 3 mm and about 9 mm.

Figure 9:
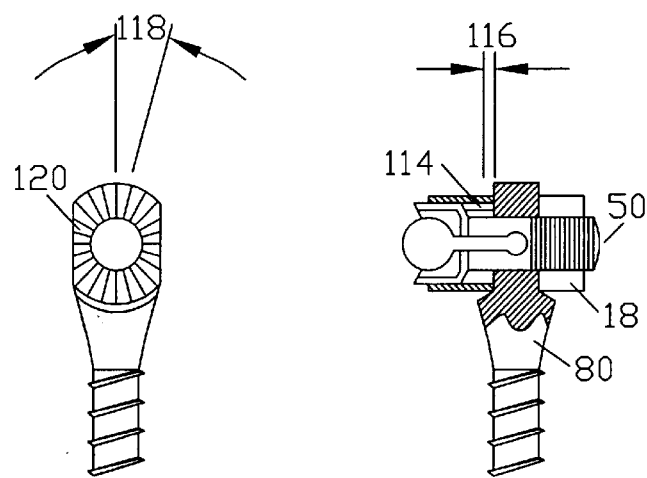
FIG. 9 depicts a front view and side view partially in section of a bone screw having radially-spaced protrusions in accordance with the present invention.

The spacer may contain a tapered cavity for receiving connector 16 as illustrated in FIG. 9. In an embodiment, the spacer contains a first plurality of protrusions or teeth that are adapted to form an engagement with a second plurality of protrusions or teeth 120 disposed on a surface of a fixation device. The teeth of the spacer and the teeth of the fixation device preferably are radially spaced at a fixed spacing 118. The teeth of the spacer and the protrusions of the fixation device preferably form a complementary fit such that adjacent, opposing teeth contact one another over interface length 116 when fastener 18 is tightened. The complementary engagement of the teeth preferably inhibits and/or prevents the fixation device from rotating As about spacer 114, thereby fixing the angle formed between the fixation device and the spinal rod.

Figure 10C:
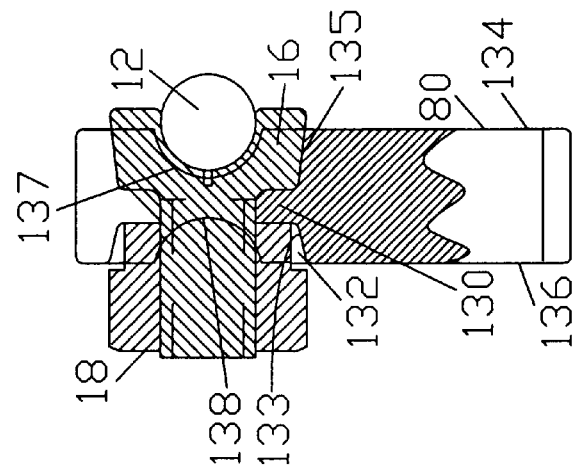
FIG. 10 depicts a front view and a side view partially in section of a reversible fixation component constructed according to teachings or the present invention.
Figure 10B:
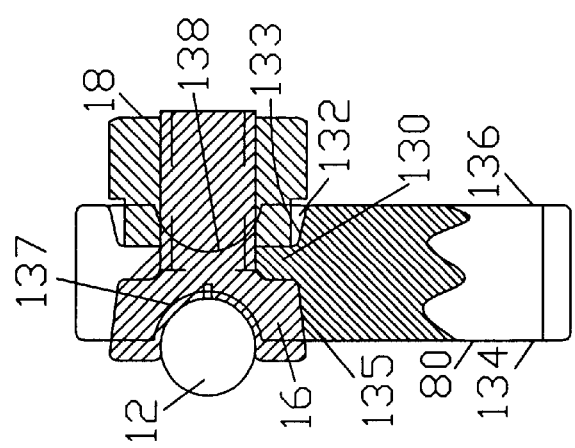
Figure 10A:
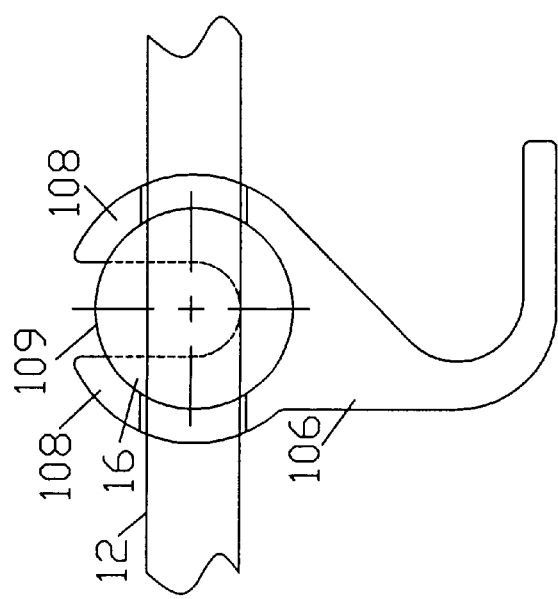

An embodiment including a reversible fixation device is illustrated in FIG. 10. The body 80 of the hook preferably includes a first U-shaped yoke 137 disposed on a first side 134 of the body and a second U-shaped yoke 138 disposed on a second side 136 of the body. A cavity 132 preferably extends through the body from the first side 134 to the second side 136. The cavity preferably contains a pair of tapered inner surfaces 133 and 135 that taper in opposite directions such that the cavity narrows in a direction from the first side 134 to the middle of the cavity and narrows in a direction from the second side 136 to the middle of the cavity. The tapered inner surfaces preferably each terminate in an engaging portion 130 disposed in the middle of the cavity. Connector 16 may be positioned within the cavity so that the receiving end extends from either first side 134 as shown in FIG. 10B or from second side 136 as shown in FIG. 10C. Thus, the reversible hook may be mounted so that either first side 134 or second side 136 is proximate the spinal rod, with the hook directed toward either the caudal or cranial direction in each case. The fixation component may contain a slot 109 through which the fastening end of the connector may be inserted during assembly of the construct. The engaging portion 130 preferably engages the outer surface of the receiving end to limit the extent to which the receiving end may be inserted into cavity 132. Fastener 18 preferably engages body 80 proximate the engaging portion.

Figure 11:
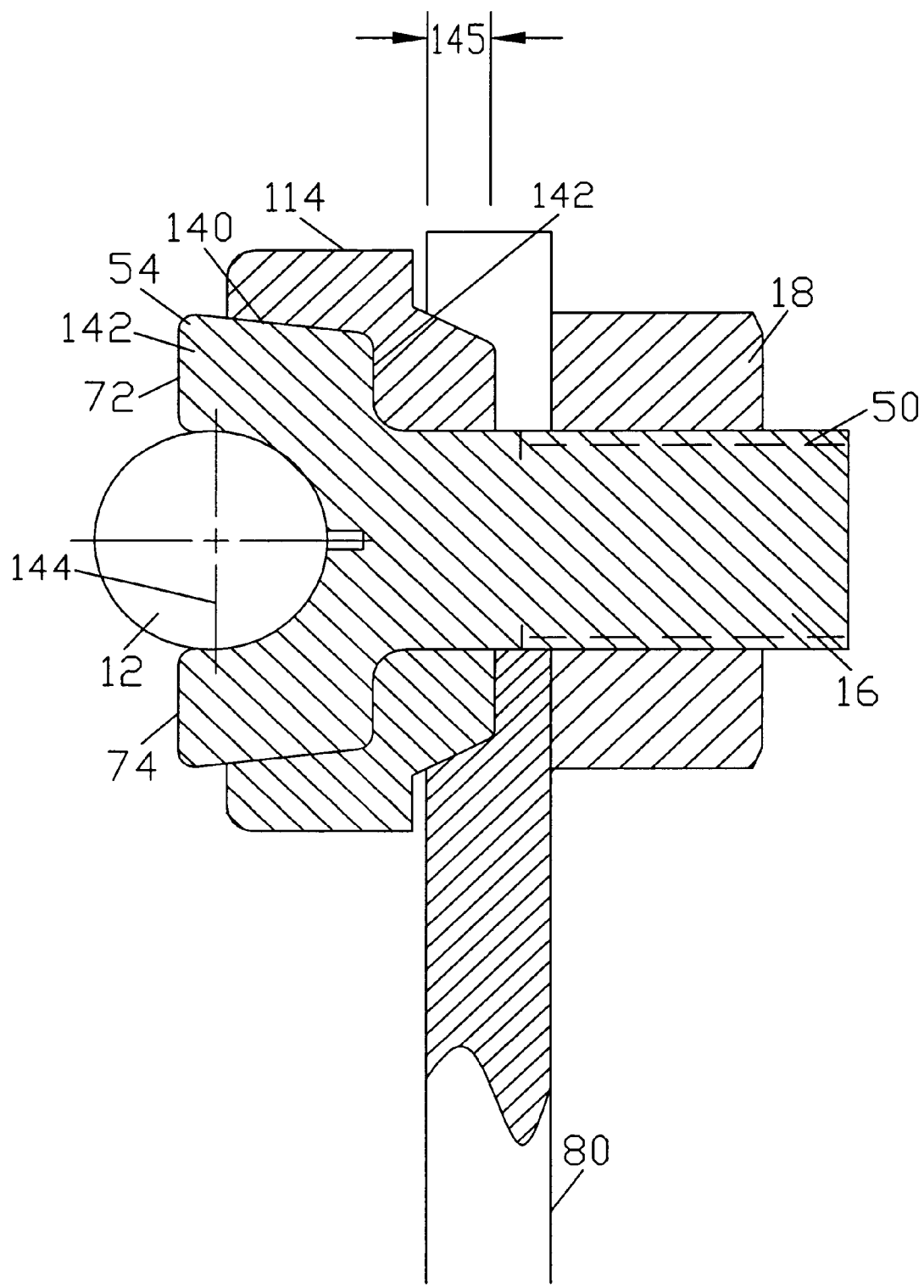
FIG. 11 depicts a side view partially in section of a spacer disposed between a spinal rod and a fastener in accordance with the present invention.

An alternate embodiment including a spacer 114 is illustrated in FIG. 11. The spacer preferably surrounds a portion of connector 16 and contains a tapered surface 140 corresponding to the outside surface of the arms of the receiving end. As fastener 18 is tightened, the connector is preferably drawn within the spacer whereby surface 140 engages and exerts a clamping force against the outer surface of the receiving end. A tensile force created by the tightening of fastener 18 preferably maintains the spacer in a fixed position between body 80 and the spinal rod. The tapered surface 140 may terminate in an engaging surface 142 that engages the receiving end, thereby limiting the extent to which the receiving end may be drawn within the spacer. The receiving end preferably forms a "pinch clamp" about the spinal rod, wherein the tips 72 and 74 of the arms terminate slightly beyond a vertical axis 144, which extends through the center of the spinal rod. The fastener may be fully tightened to create a selected offset length 145 that is preferably between about 2 mm and about 10 mm.

To surgically install spinal fixation system 10, the threaded end of connector 16 is preferably inserted through the tapered cavity of a spinal fixation component and fastener 18 is loosely threaded onto the threaded end. The spinal fixation component is then attached to the spine via a hook or screw in a selected location. A plurality of spinal fixation components may be attached to the spine in like manner. Spinal rod 11 may be contoured to match the desired curvature of the spine and placed into the surgical opening. The spinal rod is preferably snapped within the borehole of the connector of each spinal fixation component. The spine is preferably manipulated such that each of the vertebra is at a selected angle and height relative to neighboring vertebrae and then each fastener 18 is fully tightened to fixably secure the spinal rod into the borehole of each connector and to secure each of the spinal fixation devices at a selected angle relative to the spinal rod. It is generally preferred that the only assembly of system components that occurs within the surgical wound is (a) the snapping of the spinal rod within one or more connectors and (b) the final tightening of one or more fasteners that have already been engaged with the fastening end. Each of the fasteners is preferably tightened with a torque of at least 150 lb-in. One or more transverse connectors may be added across neighboring spinal rods for support to increase the strength of the overall construct and maintain the spinal rods at a fixed distance from one another.

In an alternate embodiment, each connector and spinal fixation component can be pre-assembled on the spinal rod prior to the implantation of the rod into the surgical wound. A connector may first be snapped onto the spinal rod. A fixation component may be added onto the connector such that the fastening end of the connector extends through the tapered cavity and the arms of the receiving end contact the inner surface of the tapered cavity. The fastener is preferably positioned on the fastening end and partially tightened to maintain the connector and fixation component engaged with the spinal rod. The fastener is preferably loosely secured on the fastening end to allow the connector and fixation component to slide along the length of the rod when a selected force is applied to the connector. The spinal rod may be contoured as necessary, and the pre-assembled system may be inserted within the surgical wound. The location of the spinal fixation components may be adjusted along the length of the rod as necessary, and the construct may be connected to the spine via fixation devices. Once a fixation component is placed at a selected location, its corresponding fastener may be fully tightened to fix its location. Fixation components may be added to or deleted from the construct as necessary without altering the position of the spinal rod or other fixation components.

In an alternate embodiment, the system may be partially pre-assembled such that a number of connectors are initially snapped onto the spinal rod. Fixation components may be inserted within the surgical wound and connected to the spine at selected locations via fixation devices. The rod may be selectively contoured and inserted within the surgical wound and aligned proximate the spine. A connector is preferably slid along the rod to a selected location proximate a fixation component on the spine, and the fastening end of the connector is inserted through the tapered cavity of the fixation component. A fastener may be placed on the fastening end to clamp the connector onto the spinal rod and to secure the fixation component therebetween. Additional connectors and fixation components may be secured to the spinal rod in like manner.

After the rod is implanted into the surgical wound, it may be necessary to add or delete a fixation component. Conventional systems tend to require that the spinal rod be removed from the surgical wound to allow a fixation component to be threaded onto or removed from the rod. In addition, fixation components of conventional systems may have to be removed from the construct to slide the added fixation component to a selected position. Connector 16 is preferably snapped onto the spinal rod at a selected location. Thus, a connector and any fixation device (e.g., screw, hook, transverse connector) may be added to the spinal rod without removing fixation components from the spinal rod or removing the spinal rod from the surgical C wound. In the same manner, a connector and fixation device may be removed from the spinal rod without altering the position of the spinal rod or adjacent connectors. The fastener 18 may be loosened and a tool may be used to unclamp the receiving end of the connector from the spinal rod, thereby eliminating the need to slide the component off the end of the spinal rod as in some conventional systems.

An embodiment of a spinal fixation system that is assembled with a threadless wedge is depicted in FIG. 12 and FIG. 13. FIG. 12 depicts the spinal fixation system prior to assembly. The spinal fixation system preferably includes connector 216 for attaching spinal rod 12 to fixation component body 80. Connector 216 preferably includes a receiving end that includes a pair of deflectable arms forming a substantially U-shaped borehole for receiving the spinal rod as in the above described embodiments. The outer surface of the receiving end may be tapered to complement the tapered inner surface of the cavity disposed within the fixation component. The outer surface of the receiving end and the tapered inner surface may be substantially flat. It is to be understood that the outer surface of the connector may be untapered while the inner surface of the cavity is tapered, or alternatively, the outer surface of the connector may be tapered while the inner surface of the cavity is untapered. The end of the connector opposite the receiving end may be capped as shown in FIG. 12.

An instrument 200 is preferably used to move the connector through the cavity to cause the arms of the connector to clamp against the spinal rod to secure it within the borehole. The instrument is preferably a pair of assembly pliers that includes a first member 202 and a second member 204. Members 202 and 204 are preferably substantially elongated and capable of moving relative to one another to apply a compressive force onto components of the spinal fixation system to assemble the components. The members are preferably connected together via hinge 206. The hinge may include a pivotal connector (e.g., bolt) about which the members can pivot relative to one another.

One of the members preferably includes an indention 210 for engaging the spinal rod. The indention preferably has a curvate shape that conforms to the shape of the spinal rod. The other member preferably includes a bore 208 that is sized to receive the end of the connector. Bore 208 preferably has a width that is greater than that of the end of the connector such that the end is capable of passing into or through the bore. Member 204 preferably includes contacting sections 214 that surround bore 208 for engaging the fixation component. FIG. 13 depicts the spinal fixation system after assembly. Member 202 preferably engages the spinal rod at indention 210, while member 204 engages the fixation component with contacting sections 214. The handles of instrument 200 are preferably squeezed together to decrease the distance between members 202 and 204, thereby forcing the connector to move within the cavity of the fixation component. The end of the connector preferably moves through the cavity and into bore 208 whereby second member 204 does not inhibit the movement of the connector through the cavity. A locking taper engagement between the connector and the spinal rod is preferably formed, and then instrument 200 may be removed from the assembly. In an alternate embodiment, member 202 engages the tips of the arms of the connector rather than the spinal rod.

In an embodiment depicted in FIG. 14, the fixation component includes a bore 222 through its top surface that communicates with the fixation component cavity. A locking element 220 is preferably inserted into bore 222 to inhibit movement of the connector within the fixation component cavity after the connector has been secured therein. Locking element 220 is preferably a set screw. Bore 222 is preferably threaded for engaging threads on the set screw. The locking element may engage the connector proximate indention 218 disposed on the outer surface of the connector.

Figure 15:
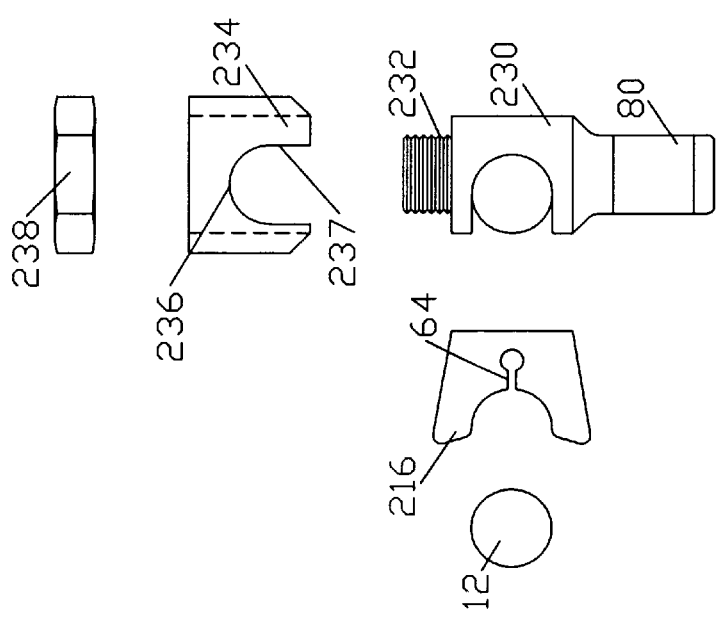
FIG. 15 depicts a spinal fixation system that includes a locking sleeve.

In an embodiment depicted in FIG. 15, fixation component 230 preferably includes a tapered cavity for receiving connector 216 as in the above described embodiments. The fixation system preferably includes a sleeve 234 that is adapted to fit about the body of the fixation component. The sleeve is preferably substantially cylindrical and may substantially surround the fixation component body. The sleeve preferably includes a substantially U-shaped opening 236 sized to permit spinal rod 12 to pass therethrough. The U-shaped opening is preferably substantially offset from the center of the sleeve as shown in FIG. 15. Opening 236 may include an angled interior locking surface 237 for engaging the spinal rod. Fixation component 230 preferably includes a fastening end 232 on its top. Fastening end 232 preferably includes threading. A fastener 238 is preferably securable to the fastening end. Fastener 238 is preferably a nut that includes threading that complements the threading on the fastening end.

Figure 17:
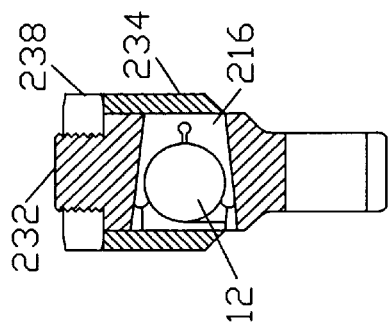
FIG. 17 depicts a side view partially in section of the system of FIG. 15 after assembly.
Figure 16:
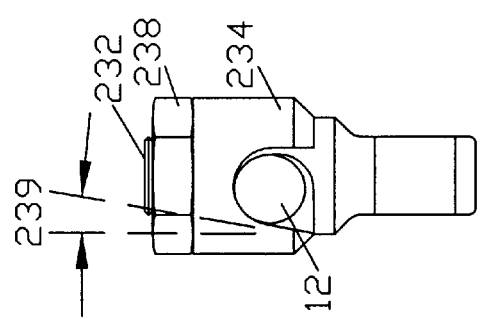
FIG. 16 depicts a side view of the spinal fixation system of FIG. 15 after assembly.

FIG. 16 depicts a side view of the spinal fixation system after assembly, and FIG. 17 depicts a cross sectional view of the assembled spinal fixation system. To assemble the system, the spinal rod is preferably snapped into the borehole of connector 216. A circumferential portion of the spinal rod preferably extends from the opening in the connector. The connector having the spinal rod disposed therein is then preferably positioned within the cavity of the fixation component. Sleeve 234 is preferably slid over fastening end 232 and around the body of the fixation component until locking surface 237 contacts the spinal rod. Fastener 238 may be threaded onto the fastening end such that the bottom surface of the fastener contacts the top of sleeve 234. Rotation of the fastener preferably downwardly translates the fastener along the fastening end and forces sleeve 234 down along the body of the fixation component. The angle 239 of locking surface 237 from a vertical axis allows the downward motion of the sleeve to impart a force on the spinal rod in a direction axially through the tapered cavity. Angle 239 preferably ranges from about 10 to 30 degrees. The distance that connector 216 moves within the tapered cavity is preferably a function of the degree to which fastener 238 is tightened. It is preferred that a locking taper engagement is formed between the connector and the fixation body cavity after fastener 238 is tightened.

Figure 18:
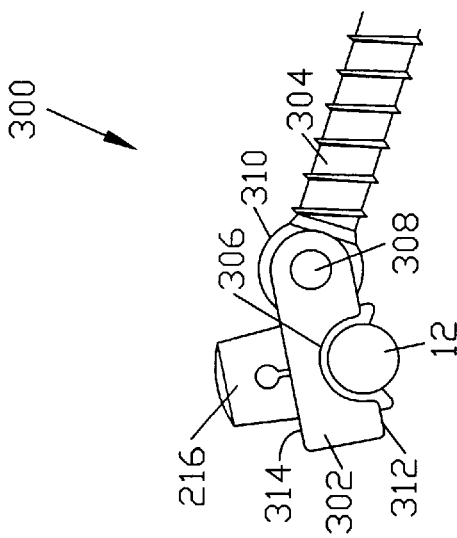
FIG. 18 depicts a side view of a spinal fixation system that includes a rotatable fixation device.

In an embodiment, depicted in FIG. 18, fixation component 300 preferably includes a body 302 and a fixation device 304. The body 302 preferably includes a cavity 318 (shown in FIG. 19) adapted to receive a connector 216. The body 302 may include a substantially U-shaped indentation 306 adapted to permit a portion of spinal rod 12 to rest within the indentation. The indentation 306 preferably runs along the bottom 312 of the body 302 in a direction substantially perpendicular to the longitudinal axis of the fixation device 304. The body 302 may include a bore (not shown) that communicates with the cavity 318. A locking element is preferably inserted into the bore to inhibit movement of the connector 216 within the C body cavity 318 after the connector has been secured therein.

The body 302 is preferably adapted to hold a fixation device 304. The fixation device 304 preferably includes a head 310. The head 310 may be semi-spherical in shape. An opening (not shown) may extend through the central portion of the head 310, at a position equidistant from any position along the semi-spherical portion of the outside surface of the head. The fixation device may a bone screw (as shown), hook, traverse connector, or similar device. The body 302 may include a cavity 318 (shown in FIG. 19) adapted to contain a portion of the head 310. A substantially cylindrical pin 308 is preferably positionable within the head 310 and the body 302 such that the fixation device 304 may be rotated about the pin 308 along the longitudinal axis of the body. The pin 308 may inhibit movement of the fixation device 304 in a direction perpendicular to the longitudinal axis of the body 302. The pin 308 may be a rivet or a screw. The pin 308 may be substantially hollow.

Figure 19:
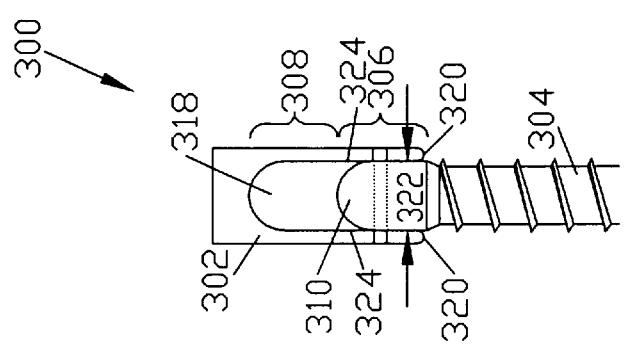
FIG. 19 depicts a top view of a fixation component that includes a rotatable fixation device.

FIG. 19 depicts a top view of the fixation component 300. The cavity 318 may be substantially U-shaped and include a front section 306 and a rear section 308. The front section 306 is preferably adapted to receive the fixation device 304. The front section 306 preferably includes at least two substantially flat arms 320 which extend out from the rear section 308. The arms 320 are preferably oriented on opposing sides of the body 302. The distance 322 between the two arms 320 may be substantially greater than the width of the head 310 of the fixation device 304. It is generally preferred that the distance 322 between the two arms 320 and the width of the head 310 be equal.

In another embodiment, the head 310 of the fixation device 304 may have at least two substantially flat edges 324. The distance 322 between the two arms 320 is preferably substantially the same as the width of the head 310 between the edges 324. The edges 324 are preferably oriented on opposing sides of the head 310. The fixation device 304 may be mounted within the cavity 318 such that the edges 324 are contained by the arms 320 of the body 302. The arms 320 may interact with the edges 324 such that movement in a direction perpendicular to the longitudinal axis of the body 302 is inhibited.

Figure 20:
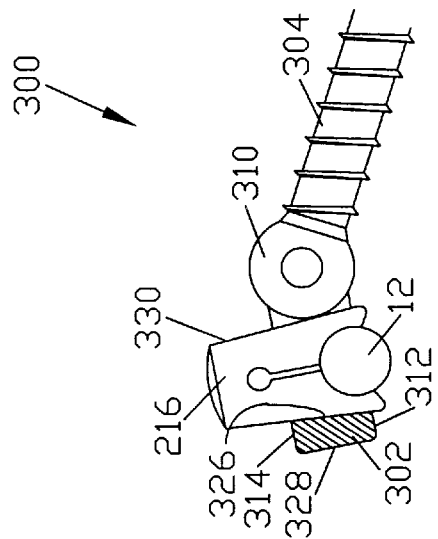
FIG. 20 depicts a cross sectional view of the side of a spinal fixation system that includes a rotatable fixation device.

The rear section 308 of the cavity 318 is substantially rounded and adapted to receive a connector 216. FIG. 20 depicts a cross sectional view of the fixation component 300, secured to a spinal rod 12, with a connector 216 oriented within the rear section of the cavity. Connector 216 preferably includes a receiving end that includes a pair of deflectable arms forming a substantially U-shaped borehole for receiving the spinal rod, as described in previous embodiments. The width of the body 302 between the rear side 328 and the interior surface 326 of the cavity 318 is preferably variable. The distance between the rear side 328 and the interior surface 326 of the body 302 preferably becomes narrower in a direction from the top 314 toward the bottom 312. The interior surface 326 of the body 302 may be substantially flat.

The head 310 of the fixation device 304 is preferably located within the body 302 in a position such a portion of the connector 216 may be inserted between the head and the interior surface 326. Movement of the connector 216 through the bottom 312 of the body 302, in a direction toward the top 314, may allow the outer edges 330 of the connector to engage the interior surface 326 of the body and the head 310 of the fixation device 304. As the connector 216 is moved further toward the top 314 of the body 302, a compressive force may be exerted by the interior surface 326 and the head 341 upon the connector. The magnitude of the compressive force may be varied as the position of the connector 216 is varied within the cavity. The compressive force preferably secures spinal rod 12 within the U-shaped borehole of the connector 216. The compressive force may inhibit rotation of the fixation device 304. Instrument 200 (not shown) may be used to position the connector 216 within the body 302 in a position which preferably secures the spinal rod to the connector. The connector 216 may be positioned within the body 302 such that the spinal rod 12 is secured within the connector, and the rotation of the fixation device 304 is inhibited.

FIG. 18 depicts a view of an assembled spinal fixation assembly. To assemble the system the spinal rod 12 is snapped into the borehole of connector 216. A circumferential portion of the spinal rod 12 preferably extends from the borehole in the connector 216. The connector 216 having the spinal rod 12 disposed therein is then preferably positioned within the body 302. The fixation device 304 may be rotated about the pin 308 until the desired angle between the body 302 and the fixation device is achieved. The angle may be varied in a direction toward the top 314 through an arc of at least 90 degrees or toward the bottom 312 through an arc of at least 90 degrees. The connector 216 may then be moved further within the body 302. As the connector 216 is moved, the head 310 and the interior surface 326 of the body 302 may impart a force upon the connector (as shown in FIG. 20) causing the arms of the borehole to compress. In this manner the connector 216 may be secured onto the spinal rod 12. The force may also inhibit further rotation of the fixation device 304. The magnitude of the force is preferably a function of the distance that the connector 216 is placed within the body 302. Instrument 200 may be used to position the connector 216 within the body 302.

Figure 21:
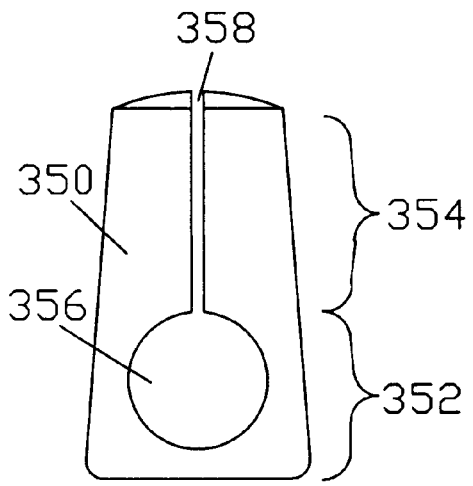
FIG. 21 depicts a side view of a tapered connector adapted to completely surround a portion of a spinal rod.

An embodiment of a connector 350 is depicted in FIG. 21. The connector 350 is adapted to secure fixation components to a spinal rod. The substantially conical connector 350 includes a receiving section 352 and an upper section 354. The receiving section 352 preferably includes a substantially circular opening 356. The opening 356 is preferably adapted to receive a spinal rod (not shown) such that the receiving section 352 of the connector 350 substantially surrounds the circumferential portion of the spinal rod. The upper section 354 preferably includes a slot 358 extending longitudinally through the center of the upper section. The slot 358 may extend from the top of the connector to the opening 356, the slot communicating with the opening.

A spinal rod is preferably axially positioned within the opening 356 by passing the spinal rod through opening. Slot 358 preferably enables the circumference of opening 356 to be altered. Insertion of the spinal rod into opening 356 results in a slight widening of at least a portion of the slot 358. In this manner, the circumference of opening 356 may be increased by an amount sufficient to allow the insertion of the spinal rod through opening 356. If the diameter of the spinal rod is slightly greater than that of the opening 356, the slot 358 may remain slightly widened after the spinal rod is inserted into the opening. It is generally preferred that the diameter of the spinal rod and the diameter of the opening 356 be equal.

Figure 22:
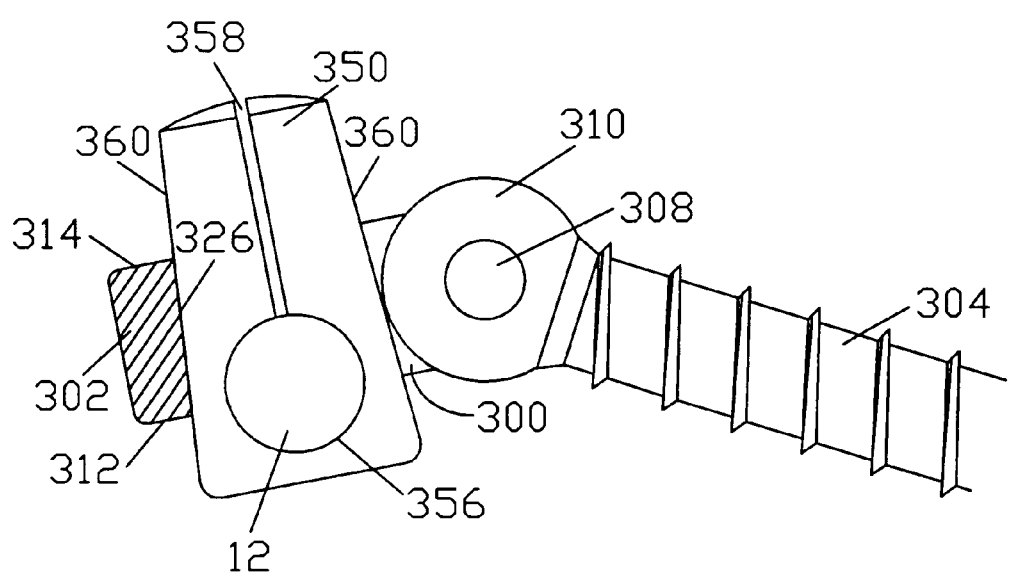
FIG. 22 depicts a cross sectional view of the side of a spinal fixation system that includes a rotatable fixation device and a connector adapted to completely surround a portion of a spinal rod.

FIG. 22 depicts a cross sectional view of an assembled spinal fixation assembly including a connector 350 and a fixation component 300. Movement of the connector 350 through the bottom 312 of the body 302, in a direction toward the top 314, may allow the outer edges 360 of the connector to engage the interior surface 326 of the body and the head 310 of the fixation device 304. As the connector 350 is moved further toward the top 314 of the body 302, a compressive force may be exerted by the interior surface 326 and the head 310 upon the connector. The magnitude of the compressive force may be varied as the position of the connector 350 is varied within the cavity. The compressive force preferably forces slot 358 to narrow, thereby securing spinal rod 12 within the opening 356 of the connector 350. The compressive force may inhibit rotation of the fixation device 304. Instrument 200 (not shown) may be used to position the connector 350 within the body 302 in a position which preferably secures the spinal rod 12 within the connector. The connector 350 may be positioned within the body 302 such that the spinal rod 12 is secured within the connector, and the rotation of the fixation device 304 is inhibited.

To assemble the system depicted in FIG. 22 the spinal rod 12 is inserted into the opening 356 of connector 350. A circumferential portion of the spinal rod 12 preferably is completely surrounded by the connector 350. The connector 350 having the spinal rod 12 disposed therein is then preferably positioned within the body 302. The fixation device 304 may be rotated about the pin 308 until the desired angle between the body 302 and the fixation device is achieved. The connector 350 may then be moved further within the body 302. As the connector 350 is moved, the head 310 and the interior surface 326 of the body 302 may impart a force upon the connector causing the slot 358 of the connector to narrow. In this manner the connector 350 may be secured onto the spinal rod 12. The force may also inhibit further rotation of the fixation device 304. The magnitude of the force is preferably a function of the distance that the connector 350 is placed within the body 302. Instrument 200 may be used to position the connector 350 within the body 302.

Figure 23:
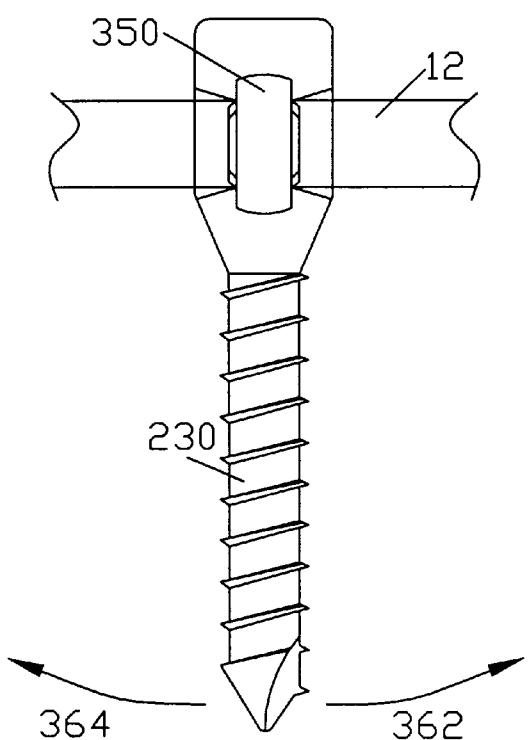
FIG. 23 depicts a rear view of a spinal fixation system adapted to completely surround a portion of a spinal rod.

In an embodiment depicted in FIG. 23, fixation component 230 may be adapted to receive connector 350. Connector 350 preferably includes an opening 356 for receiving the spinal rod 12 and a slot 358 (shown in FIG. 24) as in the above described embodiments. The fixation component 230 preferably can be pivoted in either direction 362 or direction 364 such that an oblique angle between 90° and about 60° is formed between the fixation component and the longitudinal axis of the spinal rod 12 as in the above described embodiments. The fixation component 230 preferably comprises a bone screw (as shown), hook, traverse connector, or similar device.

Figure 24:
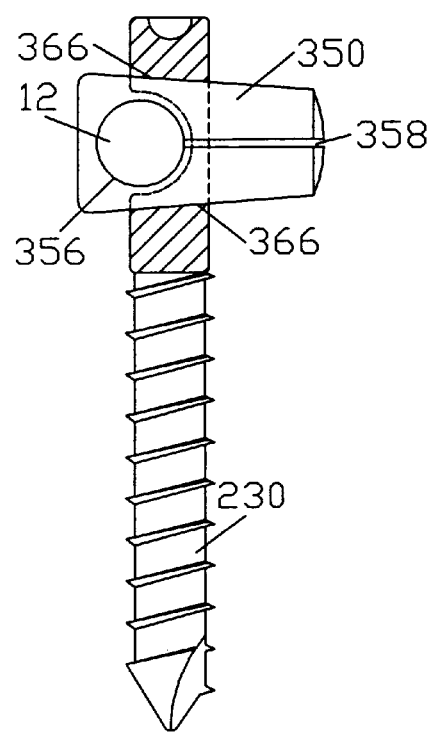
FIG. 24 depicts a cross sectional view of the side of a spinal fixation system adapted to completely surround a portion of a spinal rod.

To assemble the system, depicted in a cross section view in FIG. 24, the spinal rod 12 is preferably inserted into the opening 356 of connector 350. The connector 350 having the spinal rod 12 disposed therein is then preferably positioned within the cavity of the fixation component 230. The fixation component 230 may be rotated until the desired angle between the fixation component and the longitudinal axis of the spinal rod is achieved. The connector 350 may then be moved further within the fixation component 230. As the connector 350 is moved, the interior surfaces 366 of the fixation component may impart a force upon the connector causing the slot 358 of the connector to narrow. In this manner the connector 350 may be secured onto the spinal rod 12. The force may also inhibit further rotation of the fixation component 230. The magnitude of the force is preferably a function of the distance that the connector 350 is placed within the body 302. Instrument 200 (not shown) may be used to position the connector 350 within the body 302.

FURTHER IMPROVEMENTS

The following improvements may be used in combination with any of the features of the above-described embodiments.

Referring back to FIG. 6, the connector is shown in a locking taper engagement with the spinal rod 12. To form this locking taper engagement, the spinal rod 12 is preferably placed within opening 62 such that a "snap-fit" engagement is first formed. The "snap-fit" engagement allows the connector to be moved over the surface of the spinal rod upon receiving a distraction force. The spinal rod may be moved in a direction along the longitudinal axis of the spinal rod. The connector may also be moved in a direction perpendicular to the longitudinal axis of the spinal rod. After the connector is moved to the proper position, the fastener 18 may be tightened, forcing the fixation component 80 over the connector. In this manner the connector may become fastened to the spinal rod 12 such that further movement of the connector with respect to the spinal rod is inhibited (i.e., a locking taper engagement is formed). In general, fastening the connector to the spinal rod in this manner preferably inhibits movement of the connector along the longitudinal axis of the spinal rod and/or perpendicular to the longitudinal axis of the spinal rod.

In an embodiment, movement of the connector with respect to the spinal rod may be further inhibited by texturing either the surface of the spinal rod or the inner surface (not shown) of the connector (i.e., the surface of the connector that contacts the spinal rod). Preferably, both surfaces are textured to inhibit movement of the connector with respect to the spinal rod. During typical manufacturing procedures, the spinal rod and the inner surface of the connector may be formed as relatively smooth surfaces. While the friction between these smooth surfaces tends to be sufficient to maintain the connector in a fixed position upon the spinal rod, under stressful conditions the connector may be moved in response to the strong forces applied to the connector. By providing a textured surface, the coefficient of friction between the spinal rod and the inner surface of the connector may be increased. This increase in friction between the spinal rod and the connector may further inhibit movement of the connector with respect to the spinal rod. Such a system may be able to withstand greater distraction forces than an untextured system is able to withstand. The textured components may, therefore, be less susceptible to movement after the device has been implanted within a patient.

A number of textured surfaces may be used to increase the coefficient of friction between the inner surface of the connector and the spinal rod. In general, any process which transforms a relatively smooth surface into a roughened surface having an increased coefficient of friction may be used. Methods for forming a roughened surface include, but are not limited to: sanding, forming grooves within a surface, ball peening processes, electric discharge processes, and embedding of hard particles within a surface.

In one embodiment a plurality of grooves may be formed in the outer surface of the spinal rod or the inner surface of the connector. Preferably, a plurality of grooves is formed in both the outer surface of the spinal rod and the inner surface of the connector. The grooves may be formed in a variety of patterns, depicted in FIGS. 25a–25f. In one embodiment, grooves may be formed in the outer surface of the spinal rod along the longitudinal axis 400 depicted in FIG. 25a. Grooves may also be formed in the inner surface of the connector such that the grooves are parallel, or substantially parallel with the grooves in the spinal rod when the connector and the spinal rod are coupled together. When a textured connector and spinal rod are coupled together the longitudinal grooves may interact with each other to provide additional resistance to movement in a direction perpendicular to the longitudinal axis of the spinal rod. This resistance is preferably enhanced while the connector is fastened to the rod in a locking taper engagement as depicted in FIG. 6. While it is preferred that both the spinal rod and the inner surface of the connector be textured, texturing of only one of the surfaces may be sufficient to attain additional resistance to movement.

Figure 25A:
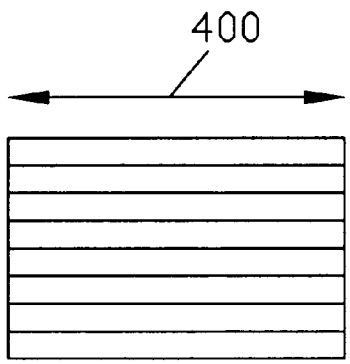
FIGS. 25a–f depict various textured patterns.
Figure 25B:
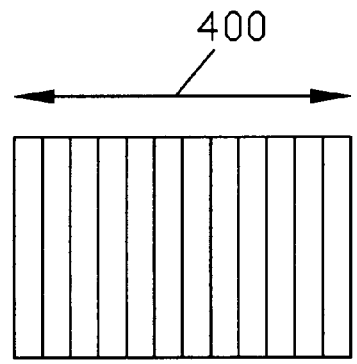
Figure 25C:
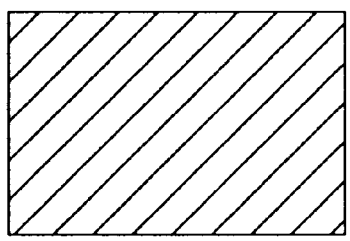
Figure 25D:
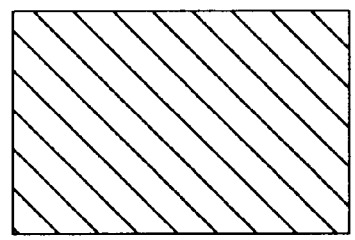
Figure 25E:
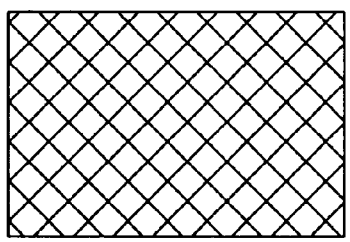

Alternately, the grooves may be formed into a pattern such that the grooves are formed perpendicular to the longitudinal axis 400 depicted in FIG. 25b. Grooves may also be formed in the inner surface of the connector such that the grooves are parallel, or substantially parallel, with the grooves in the spinal rod when the connector and the spinal rod are coupled together. When a textured connector and spinal rod are coupled together, the perpendicular grooves may interact with each other to provide additional resistance to movement in a direction along the longitudinal axis of the spinal rod. This resistance is preferably enhanced while the connector is fastened to the rod in a locking taper engagement as depicted in FIG. 6. While it is preferred that both the spinal rod and the inner surface of the connector be textured, texturing of only one of the surfaces may be sufficient to attain additional resistance to movement.

Figure 25F:
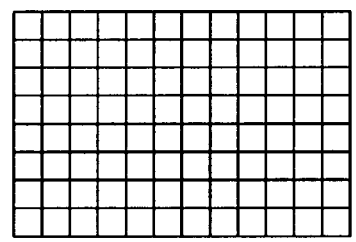

In general, the use of longitudinal or perpendicular texturing tends to provide increased resistance toward movement of the connector in a direction perpendicular to the orientation of the grooves. In order to provide increased resistance toward movement in both directions (i.e., the longitudinal direction and a direction perpendicular to the longitudinal direction) a variety of other patterns may be used. Diagonal patterns (FIGS. 25c and 25d), a grid pattern (FIG. 25f) or a diamond pattern (FIG. 25e) may be formed on the contacting surfaces of the connector and the spinal rod to enhance the resistance to movement of the connector in both the longitudinal and the perpendicular directions. When the connector and the spinal rod, both of which are textured in one of the patterns depicted in FIGS. 25a 25f are coupled together, the grooves may interact with each other to provide additional resistance to movement in either a longitudinal direction or a direction perpendicular to the longitudinal axis. This resistance is preferably enhanced while the connector is fastened to the rod in a locking taper engagement, as depicted in FIG. 6. While it is preferred that both the spinal rod and the inner surface of the connector be textured, texturing of only one of the surfaces may be sufficient to attain additional resistance to movement. Any mixed combination of diagonal, grid or diamond patterns may be used to increase the friction between the connector and the spinal rod.

In another embodiment, the frictional surface may be created by an electrical discharge process. An electrical discharge process is based on the principle of removal of portions of a metal surface by spark discharges. Typically a spark is generated between the surface to be treated and an electrode by creating potential differential between the tool and the electrode. The spark produced tends to remove a portion of the surface disposed between the electrode and the surface. Typically, the electrode is relatively small such that only small portions of the surface are removed. By moving the electrode about the surface numerous cavities may be formed within the surface. Typically these cavities are somewhat pyramidal in shape. Various patterns may be formed within the surface depending on how the electrode is positioned during the discharge. Electric discharge machines are well known in the art. A method for forming a frictional surface within a metal surface using an electric discharge process is described in U.S. Pat. No. 4,964,641 to Miesch et al. which is incorporated by reference as if set forth herein.

All of the patterns shown in FIGS. 25a–25f may be formed using an electric discharge machine. Preferably a diamond pattern or a waffle pattern is formed on the inner surface of the connector and/or the spinal rod. When the connector and the spinal rod, both of which are textured by an electric discharge process, are coupled together, the grooves may interact with each other to provide additional resistance to movement in either a longitudinal direction or a direction perpendicular to the longitudinal axis. While it is preferred that both the spinal rod and the inner surface of the connector be textured, texturing of only one of the surfaces may be sufficient to attain additional resistance to movement. Any mixed combination of diagonal, grid or diamond patterns may be used to increase the friction between the connector and the spinal rod.

In another embodiment, the inner surface of the connector and the outer surface of the spinal rod may be textured by the use of a shot peening process. A shot peening process for forming a textured surface is described in U.S. Pat. No. 5,526,664 to Vetter which is incorporated by reference as if set forth herein. In general, a shot peening process involves propelling a stream of hardened balls, typically made of steel, at a relatively high velocity at a surface. To create a pattern upon an area of the surface the stream is typically moved about the surface. The speed by which the stream is moved about the surface tends to determine the type of textured surface formed.

Preferably, the stream is moved such that a pattern resulting in a textured surface having ridges and valleys is formed on the inner surface of the connector and the outer surface of the spinal rod. When the textured connector and spinal rod are coupled together the ridges and valleys may interact with each other to provide additional resistance to movement in either a longitudinal direction or a direction perpendicular to the longitudinal axis. While it is preferred that both the spinal rod and the inner surface of the connector be textured, texturing of only one of the surfaces may be sufficient to attain additional resistance to movement.

In another embodiment the textured surface may be produced by embedding sharp hardened particles in the surface. A method for embedding sharp hardened particles in a metal surface is described in U.S. Pat. No. 4,768,787 to Shira which is incorporated by reference as if set forth herein. The method of Shira involves using a laser or other high energy source to heat the surface such that the surface melts in selected areas. Just before the molten area re-solidifies a stream of abrasive particles is directed to the area. In this manner some of the particles tend to become embedded with the molten surface. The particles typically have a number of sharp edges that protrude from the surface, after the particles have been embedded within the surface. When a connector and spinal rod, textured by this process, are coupled together the hardened particles may interact with each other or smooth portions of the surface to provide additional resistance to movement in either a longitudinal direction or a direction perpendicular to the longitudinal axis. While it is preferred that both the spinal rod and the inner surface of the connector be textured in this manner, texturing of only one of the surfaces may be sufficient to attain additional resistance to movement.

Any of the above methods of texturing may be used in combination with another method. For example, the outer surface of the spinal rod may be textured using a pattern of grooves. The connector, however, may be textured using an electrical discharge method. When coupled together the textured surfaces of the connector and spinal rod may interact with each other to provide additional resistance to movement in either a longitudinal direction or a direction perpendicular to the longitudinal axis.

Textured surfaces may also be formed on other components of the spinal implant system. In an embodiment, movement of the fixation component with respect to the spinal rod may be further inhibited by texturing either the outer surface of the connector or the inner surface 82 of the tapered cavity of the fixation component, as depicted in FIG. 5. Preferably, both surfaces are textured to inhibit movement of the fixation component with respect to the spinal rod. In embodiments when the connector and the fixation component are joined without the use of a fastening device, as depicted in FIG. 13, the friction between the outer surface of the connector and the inner surface of the tapered cavity preferably prevents the fixation component from being forced away from the spinal rod in response to a distraction force. By providing a textured surface the coefficient of friction between the outer surface of the connector and the inner surface of the tapered cavity may be increased. This increase in friction between may further inhibit movement of the fixation component with respect to the spinal rod. Such a system may be able to withstand greater distraction forces than an untextured system is able to withstand. The textured components may, therefore, be less susceptible to movement after the device has been implanted within a patient.

In another embodiment a connector 216 is disposed with a fixation component having a rotatable fixation device 304 as depicted in FIG. 20. When inserted within the cavity 318 (shown in FIG. 19) connector 216 exerts a force on head 310 of fixation device 304. This force may be sufficient to inhibit further rotation of the fixation device. To enhance this inhibition of the rotation of the fixation device 304, either an outer surface of connector 216 or the outer surface of head 310 may be textured in one of the manners described above. Preferably both surfaces are textured to enhance the inhibition of rotation.

Referring to FIG. 22, connector 350 may also be textured to prevent slipping of the connector with respect to the spinal rod 12. Preferably the inner surface of opening 356 and the spinal rod are textured by any of the methods described above. Texturing the inner surface of the opening 356 and the spinal rod 112 may provide additional resistance to movement in either a longitudinal direction or a direction perpendicular to the longitudinal axis. Additionally, the outer surface of the connector and the head 310 of the fixation device 304 may also be textured. Texturing of the outer surface of the connector and the head 310 of the fixation device 304 may provide additional resistance to rotation of the fixation device 304.

It is to be understood that any or all of the surfaces in any of the embodiments described above may textured as described. The texturing of the surfaces on any of the embodiments may be performed to enhance inhibit movement of the components after assembly.

Figure 26:
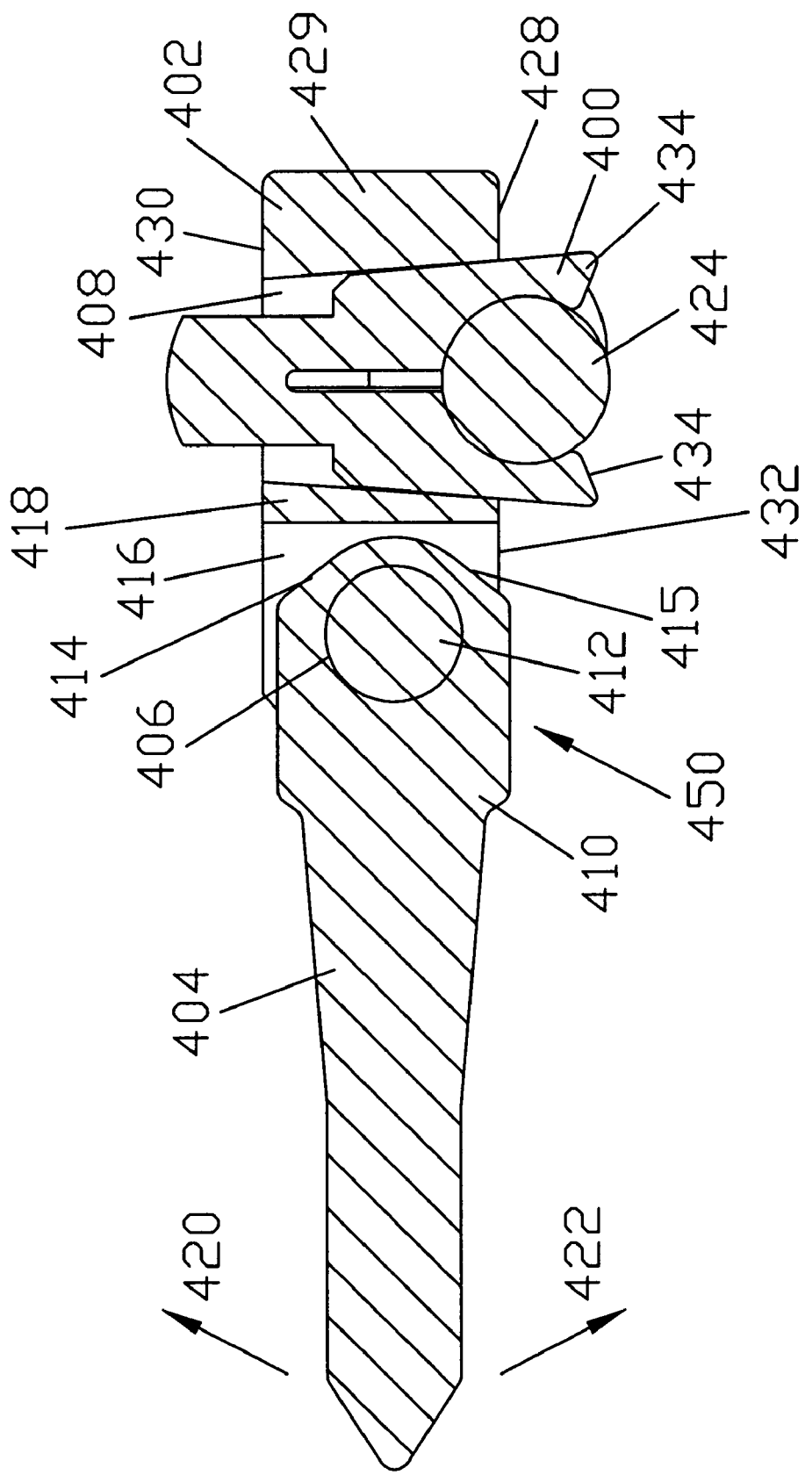
FIG. 26 depicts a cross sectional view of a spinal fixation system that includes a fixation component having two cavities.

In an embodiment, depicted in FIG. 26, a connector 400 is preferably coupled to a fixation component 450. The fixation component 450 preferably includes a body 402 and a fixation device 404. The body 402 preferably includes an upper cavity 408 adapted to receive connector 400. The body 402 may include a bore (similar to the bore shown in FIG. 14) that communicates with the upper cavity 408. A locking element may be inserted into the bore to inhibit movement of the connector 400 within the body cavity 408 after the connector has been secured therein.

The fixation component preferably includes a lower cavity 416 to hold a fixation device 404. The fixation device may be a bone screw (as shown), hook, traverse connector, or similar device for securing the fixation component to a bone. The fixation device 404 preferably includes a head 410. The head 410 may have a number of shapes including semispherical, rectangular, and pyramidal. An opening 406 preferably extends through the central portion of the head 410. A substantially cylindrical pin 412 is preferably positionable within the head 410 and the body 402 such that the fixation device 404 may be rotated about pin 412 along the longitudinal axis of the body. The pin 412 may be a rivet or a screw. The pin 412 may be substantially hollow.

The head 410 may include at least one substantially flat portions. Preferably, the head includes two substantially flat portions 414 and 415. The flat portions are formed on the head proximate the wall 418 which divides the lower cavity 416 from the upper cavity 408. The flat portions, 414 and 415, preferably interact with the wall 418 to restrict rotation of the fixation device 404. Rotation of the fixation device 404 in direction 420 preferably continues until the flat portion 414 engages wall 418. Similarly flat portion 415 engages wall 418 to restrict rotation in direction 422. Flat portions 414 and 415 of head 410 are preferably configured to allow the fixation device to be rotated about 30 degrees in either direction.

The fixation component 450 preferably includes two substantially flat arms 432 which extend out from the body in a manner similar to the arms depicted in FIG. 19. The head 410 of the fixation device 404 preferably has at least two substantially flat edges. The distance between the two arms is preferably substantially the same as the width of head 410. The fixation device may be mounted within the lower cavity 416 such that the edges are contained by the arms 432 of the body.

Connector 400 preferably is adapted to attach a spinal rod 424 to connect the spinal rod to the fixation component 450. Connector 400 preferably includes a receiving end, the receiving end including a pair of deflectable arms 434 forming a substantially U-shaped borehole for receiving the spinal rod 424, as described in previous embodiments. The outer surface of the receiving end may be tapered to complement the tapered inner surface of the upper cavity 408. The outer surface of the receiving end and the tapered inner surface may be substantially flat. It is to be understood that the outer surface of the connector may be untapered while the inner surface of the cavity is tapered. Alternatively, the outer surface of the connector may be tapered while the inner surface of the cavity is untapered. The outer surface of the connector, the inner surface of the cavity, or both of these surfaces may be textured to inhibit loosening of the connector 400 after the connector has been inserted within the fixation component 450. The texturing may be accomplished by using any of the techniques previously described.

The spinal rod 424 is preferably positioned within the U-shaped borehole of the connector 400. To secure the spinal rod within connector 400, the connector is preferably moved into the upper cavity 408 of the fixation component 450. As connector 400 is moved within the upper cavity 408 in a direction from the first end 428 to the second end 430 an interference fit is preferably created between the arms of the receiving end and the inner surface of the upper cavity. The arms of the receiving end are preferably deflected toward one another such that the slot is narrowed and the arms of the receiving end exert a compressive force against the spinal rod disposed within the borehole. In this manner a locking taper engagement may be formed between the connector, the fixation device and the spinal rod.

Figure 27:
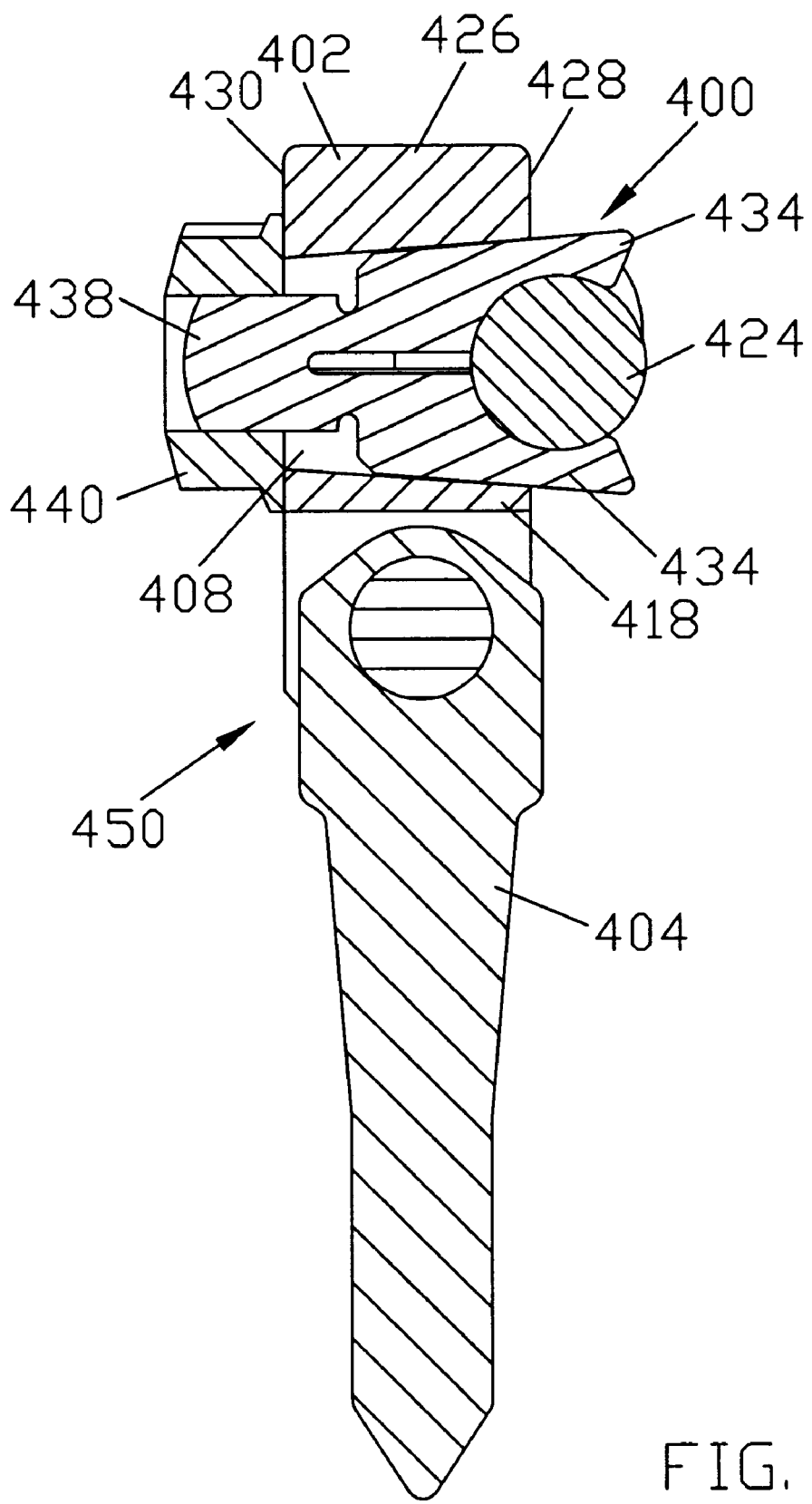
FIG. 27 depicts a cross sectional view of a spinal fixation system that includes a fixation component having two cavities, wherein the connector is secured to the fixation component by a fastener.

In an embodiment depicted in FIG. 27, a connector 400 is coupled to a fixation component 450. The fixation component 450 preferably includes a body 402 and a fixation device 404. The body 402 preferably includes an upper cavity 408 adapted to receive connector 400. The fixation device 404 is preferably rotatable as previously described. The connector preferably includes a fastening end 438 and a receiving end 436 opposite the fastening end 438. The fastening end 438 is preferably adapted to engage a fastener 440. The fastener 440 is preferably a nut. The receiving end 436 preferably includes a pair of arms 434 that together form a U-shaped borehole.

Fastener 440 may be a hex nut and preferably contains female threading, which is sized to fit male machine threads formed on the fastening end 438. The fastener 440 preferably engages fastening end 438 and body 402. Tightening of the fastener 440 preferably moves the connector within the upper cavity in a direction from first end 428 to second end 430, thereby creating an interference fit between the arms of the receiving end 436 and the inside surface of the upper cavity 408. In an embodiment where the fastener 440 is a nut, tightening of the fastener is accomplished by rotating the fastener in a tightening direction. As the fastener 440 is tightened, the arms 434 are preferably deflected toward one another such that the slot is narrowed and the arms of the receiving end 436 exert a compressive force against the spinal rod 424 disposed within the borehole.

Figure 28:
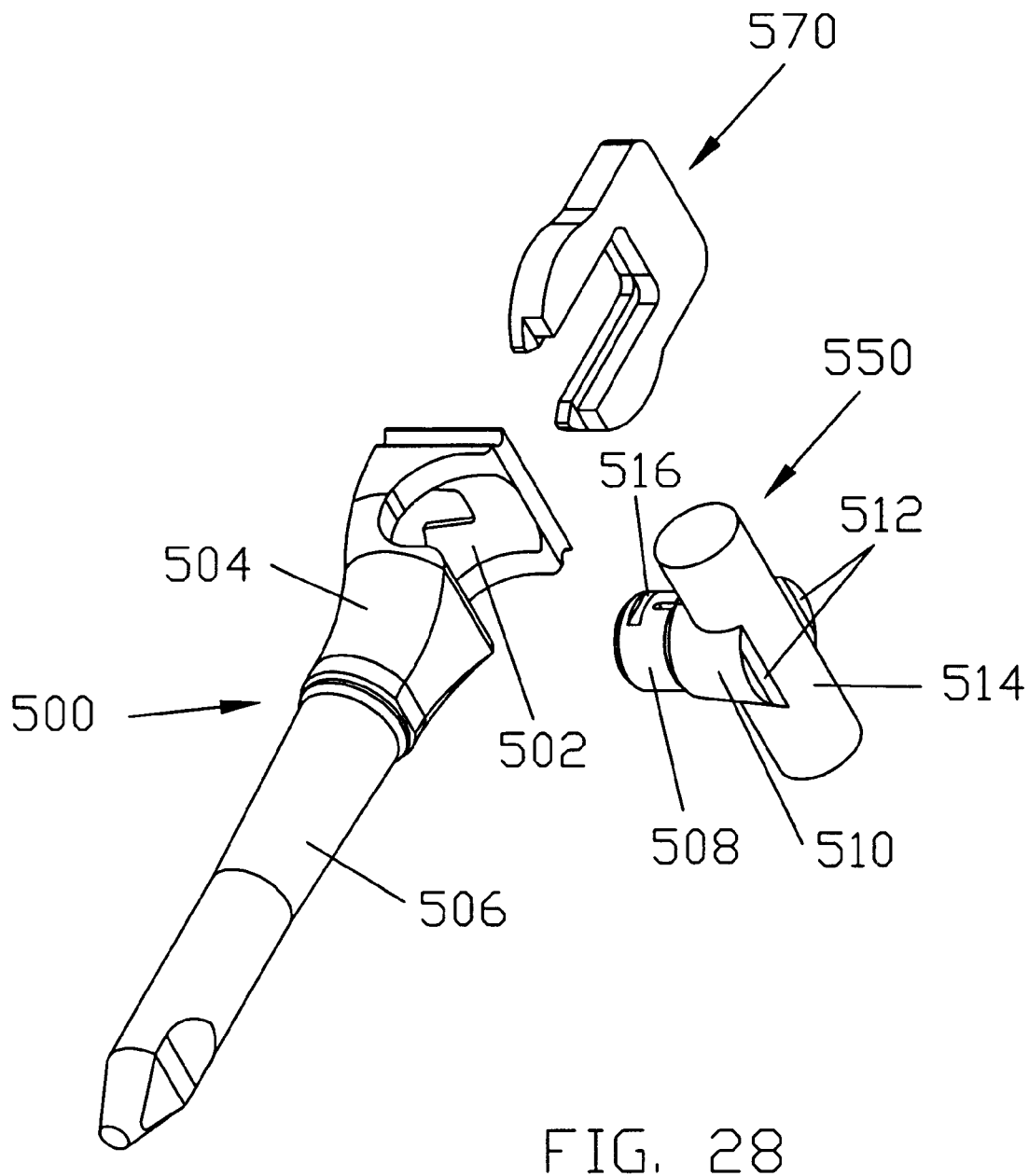
FIG. 28 depicts a perspective view of a spinal fixation system which includes a locking clip to secure the connector to the fixation component.

In an embodiment depicted in FIG. 28, fixation component 500 preferably includes a tapered cavity 502 for receiving connector 550, as in the above described embodiments. The fixation system preferably includes a clip 570 that is configured to fit about a portion of connector 550. The clip 570 is preferably configured to inhibit removal of the connector from the tapered cavity 502 after a locking taper engagement is formed. The fixation component 500 preferably includes a body 504 and a fixation device 506 coupled to the body. The body 504 preferably includes the tapered cavity 502. The fixation device may be a bone screw (as shown), hook, traverse connector, or similar device for securing the fixation component to a bone. The fixation device may be a monoaxial device (i.e., a non-rotatable device) as shown in FIG. 28 or, alternatively, the fixation device may be polyaxial device (i.e., rotatable) as described in previous embodiments.

The connector 550 preferably includes a fastening end 508 and a receiving end 510 opposite the fastening end. The receiving end preferably includes a pair of arms 512 that together form a U-shaped borehole. Spinal rod 514 is preferably positionable within the borehole.

Figure 29:
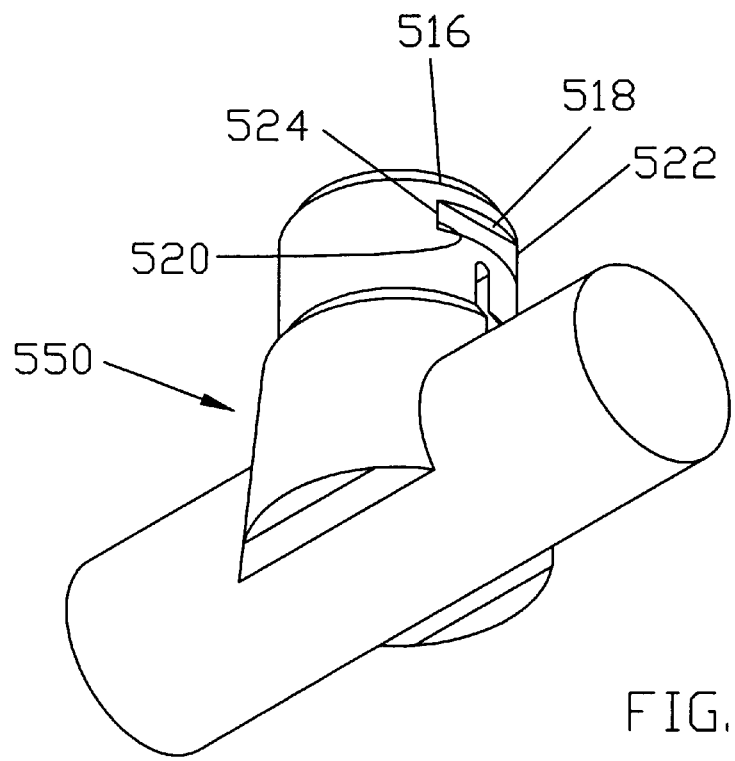
FIG. 29 depicts a perspective view of a connector, the connector including an indentation.

The fastening end 508 may include at least one indentation. Preferably, the fastening end 508 includes two indentations 516, formed on opposite sides of the fastening end. The indentation is preferably trapezoidal in shape, although other shapes may be used including square and rectangular. Turning to FIG. 29, the bottom surface and sidewalls 518 and 520 of the indentation are preferably substantially flat. The indention is preferably formed such that the distance between sidewalls 518 and 520 is variable. Preferably, the distance between sidewalls 518 and 520 proximate the first end 522 is substantially greater than the distance between the sidewalls proximate the second end 524. In this manner the indentation is substantially tapered.

Figure 30:
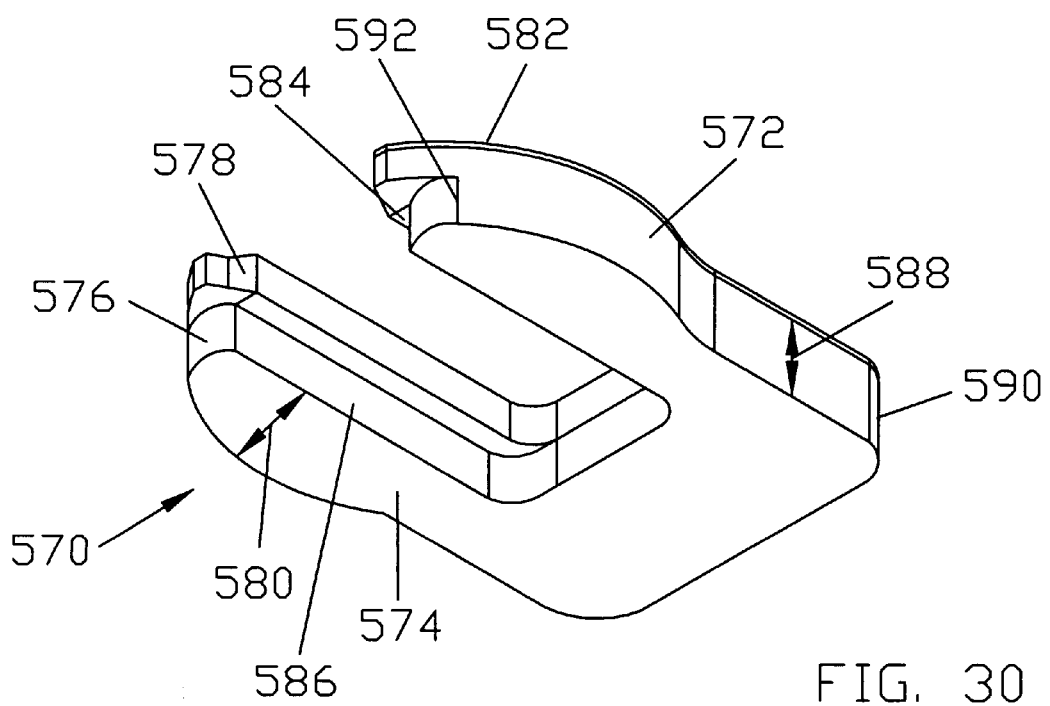
FIG. 30 depicts a perspective view of a locking clip.

The indentation is configured to couple with clip 570 to inhibit movement of the connector 550 through the fixation component 500. Referring to FIG. 30, clip 570 preferably includes two arms 572 and 574 which together define a substantially U-shaped opening. Each of the arms preferably includes an upper portion 578 and a lower portion 576. The lower portion 576 of the arms has a width 580 which is substantially less than a width of the upper portion 578. The upper portion 578 of the arm may be substantially longer than the lower portion. The lower portions 576 of each of the arms are separated from each other by a distance equal to or greater than the diameter of the connector 550.

The clip 570 is preferably coupled to the connector 550 after a locking taper engagement has been formed between the connector 550 and fixation component 500. The formation of the locking taper engagement preferably leaves a portion of the fastening end 508 extending from the fixation component 500. The indentation preferably is exposed when a locking taper engagement is formed. To inhibit further movement of connector 550, the clip 570 is positioned such that the upper portion 578 of the clip 570 engages a portion of the indentation. The clip 570 may then be positioned such that the upper portion 578 of the clip resides within the indentation 516. Preferably, positioning the clip 570 is accomplished by sliding the upper portion 578 of the clip across the bottom surface of the indentation 516. When properly positioned the top surface 582 of clip 570 engages the upper sidewall 518 of the indentation. The lower edge 584 of the upper portion 578 of clip 570 preferably engages the lower sidewall 520. The inner surface 586 of the lower portion 576 of the clip preferably engages a portion of the fastening end 508.

The clip 570 is preferably tapered in a manner complimentary to the tapering of the indentation 516. Preferably, the height 588 of clip 570 is substantially greater at the first end 590 than a height of the clip at the second end 592. The height 588 of the clip proximate the first end 590 is preferably slightly greater than a width of the indentation proximate end 522. As the clip 570 is inserted through indentation 516, an interference fit between the arms 572 and 574 of the clip and the sidewalls 518 and 522 of the indentation is preferably formed. As the clip is further inserted into the indentation the interference fit preferably becomes stronger. In this manner the clip may be secured within the indentation.

Figure 31:
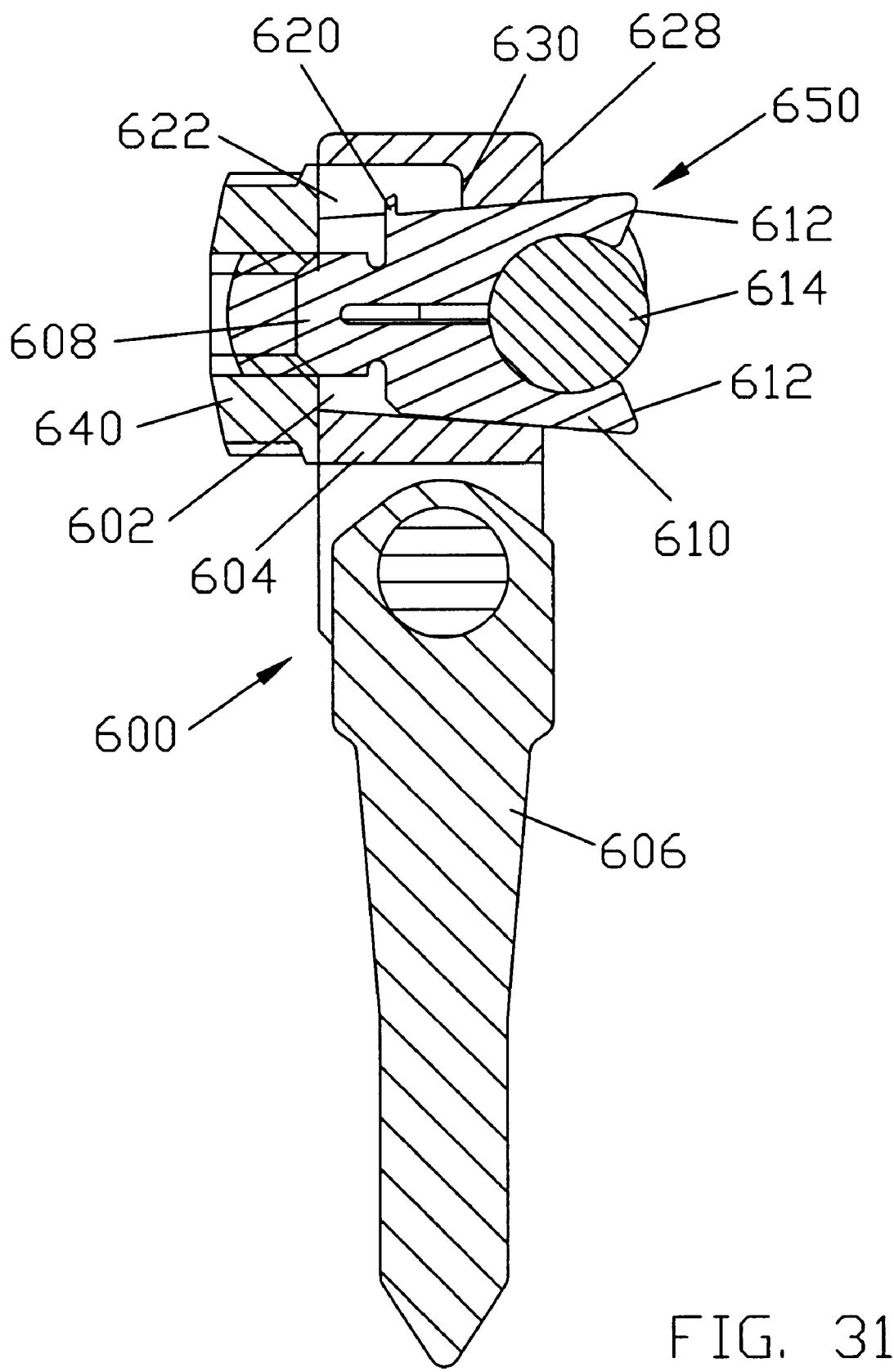
FIG. 31 depicts a cross-sectional view of a spinal fixation system which includes a connector having a locking tab.

In an embodiment, depicted in FIG. 31, fixation component 600 preferably includes a tapered cavity 602 for receiving connector 650 as in the above described embodiments. The connector 650 preferably includes a tab 620 configured to inhibit removal of the connector from the tapered cavity 502 after a locking taper engagement is formed. A tab as used herein is defined as a protrusion of any shape which extends out from a surface of a component. The fixation component preferably includes a body 604 and a fixation device 606 coupled to the body. The body 604 preferably includes the tapered cavity 602. The fixation device 606 may be a bone screw (as shown), hook, traverse connector, or similar device for securing the fixation component to a bone. The fixation device 606 may be a monoaxial device (i.e., a non-rotatable device) or, alternatively, the fixation device may be polyaxial device (i.e., rotatable) as shown in FIG. 31.

The connector 650 preferably includes a fastening end 608 and a receiving end 610 opposite the fastening end. The receiving end preferably includes a pair of arms 612 that together form a U-shaped borehole. Spinal rod 614 is preferably positionable within the borehole.

The tab 620 is preferably formed proximate the top of the receiving end 610. The tab may have a number of shapes including but not limited to rectangular, square, diamond, and triangular. Preferably, the tab is rectangular in shape. The tab 620 preferably extends out from the outer surface of the connector 550. The tab may extend over about half of the circumference of the connector. Preferably, the tab 620 extends over less than about a quarter of the circumference of the connector. A second tab (not shown) may be formed opposite the first tab.

The cavity 602 preferably contains a channel 622 for receiving tab 620. The channel 622 may be formed in either the rear wall 624 of the cavity 602 or the front wall 626 of the cavity. The channel 622 may be formed in both the front and rear portions of the cavity. The channel preferably has a width that is slightly larger than a width of the tab. When a locking taper engagement is formed the connector is positioned within the cavity such that the tab is preferably positioned within the channel. Preferably, the tab is formed on the connector such that the tap resides within a central portion of the channel, as depicted in FIG. 31, when the connector 650 is secured within the cavity 602. The connector 602 may be moved in a direction toward the first side 628 of the fixation component until the tab 620 engages the bottom edge 630 of the channel 622. The bottom edge 630 of the channel preferably prevents further movement of the connector toward first side 628. The bottom edge of the channel is preferably positioned to allow the connector to be partially moved toward the first side 628. Movement of the connector toward the first side will preferably reduce the pressure exerted by the connector upon the spinal rod. This allows the spinal rod to be repositioned within the connector without having to remove the connector from the cavity. A nut or locking clip 640 may be attached to the fastening end of the connector to inhibit removal of the connector from the tapered cavity 502 after a locking taper engagement is formed.

It is to be understood that any or all of the surfaces in any of the embodiments depicted in FIGS. 26–31 may textured as described above. The texturing of the surfaces on any of the embodiments may be performed to enhance inhibit movement of the components after assembly.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An implant system for fixation of the human spine, comprising:
    a connector comprising an upper section and a lower section, the lower section defining an opening, the upper section defining a slot communicating with the opening, the opening comprising a textured inner surface;
    a spinal rod axially positionable through the opening during use, wherein the spinal rod is fixable within the opening by a clamping force exerted by the connector; and
    a fixation component comprising a body, the body comprising a tapered cavity, the tapered cavity comprising an inner surface, a first end and a second end, wherein the tapered cavity narrows in a direction from the first end to the second end, and wherein the connector is configured to be at least partially disposed within the tapered cavity such that the inner surface of the tapered cavity engages and exerts a compressive force onto an outer surface of the connector to maintain the spinal rod within the opening during use, and wherein the connector is moveable within the tapered cavity to cause a width of the opening to narrow during use;
    and wherein the textured inner surface of the opening of the connector engages with the surface of the spinal rod during use such that movement of the connector with respect to the spinal rod is substantially inhibited during use.

2. The implant system of claim 1 wherein the opening has a width that is adjustable by moving the connector within the tapered cavity.

3. The implant system of claim 1 wherein the lower section comprises a first arm having a first tip and a second arm having a second tip, the first arm and the second arm together defining the opening such that the opening is substantially U-shaped, and wherein the slot enables the first arm and the second arm to be deflected relative to one another during use, the deflection of the arms causing a change in a distance between the first tip and the second tip during use.

4. The implant system of claim 1 wherein the fixation component further comprises a bore, and further comprising a locking element configured to extend through the bore and contact the connector to inhibit movement of the connector within the tapered cavity during use.

5. The implant system of claim 1 wherein the outer surface of the lower section has a taper that complements that of the tapered cavity.

6. The implant system of claim 1 wherein the compressive force exerted against the spinal rod is selectively variable and is a function of a depth of the lower section within the tapered cavity.

7. The implant system of claim 1 wherein the fixation component further comprises a fixation device for attaching the spinal rod to a vertebra.

8. The implant system of claim 1 wherein the body comprises a substantially U-shaped yoke having an axial length, the yoke being formed between a top section of the body and a bottom section of the body, the top section of the body comprising a first edge, the bottom section of the body comprising a second edge, the first and second edges defining a width of the yoke, and wherein the first and second edges are curved such that the width of the yoke varies across the axial length of the yoke.

9. The implant system of claim 1 wherein the fixation component further comprises a fixation device and a spacer configured to fit between the connector and the fixation component during use, the fixation device comprising protrusions, the spacer offsetting the fixation device from the spinal rod and comprising teeth configured to form a complementary engagement with the protrusions to inhibit rotation of the fixation device about the spacer during use.

10. The implant system of claim 1 wherein the body further comprises a top section and a bottom section, the tapered cavity being formed in between the top section of the body and the bottom section of the body, the top section of the body and the bottom section of the body each comprising edges that are curved, and wherein the fixation component is configured to pivot about the spinal rod in a substantially vertical plane during use, and wherein the curved edges are configured to contact the spinal rod during the pivoting of the fixation component, thereby defining a range of pivotal motion of the fixation component during use.

11. The implant system of claim 1 wherein the fixation component further comprises a transverse connector for connecting the spinal rod to a neighboring spinal rod, the transverse connector comprising a reduced section and a beveled section, the reduced section having a width less than a width of the body, the beveled section being located between the body and the reduced section, and wherein the reduced section comprises a bend to shorten a lateral distance between the spinal rod and the neighboring spinal rod.

12. The implant system of claim 1 further comprising a fastener configured to engage the body and the upper section of the connector, the fastener being configured to secure the connector and the fixation component together.

13. The implant system of claim 1 wherein a portion of the upper section is threaded, and further comprising a nut configured to engage the threaded portion of the upper section of the connector, and wherein the nut is configured to cause movement of the lower section within the tapered cavity during use such that the opening exerts a compressive force against the spinal rod to maintain the spinal rod within the opening.

14. The implant system of claim 1 wherein the spinal rod is positioned within the opening during use such that a portion of the spinal rod is exposed from the lower section of the connector.

15. The implant system of claim 1, further comprising a sleeve comprising a substantially U-shaped opening, the sleeve being configured to fit substantially about the body of the fixation component during use, and wherein the sleeve comprises an interior surface that is configured to impart a force onto the spinal rod when the sleeve is downwardly translated along the body, the force causing the connector to move into the tapered cavity during use.

16. The implant system of claim 1 wherein the opening substantially surrounds a circumferential portion of the spinal rod during use.

17. The implant system of claim 1 wherein movement of the connector in a direction from the first end to the second end causes a portion of the slot to narrow such that the lower section exerts a compressive force against the spinal rod to clamp the spinal rod within the opening during use.

18. The implant system of claim 1 wherein the fixation component further comprises a fixation device, the fixation device comprising a head, and wherein a portion of the head is positioned within the cavity, and wherein the head is positioned within the cavity such that the fixation device is rotatable along a longitudinal axis of the body during use, and wherein the connector is positionable within the cavity such that rotation of the fixation device is substantially inhibited during use.

19. The implant system of claim 1 wherein the spinal rod is substantially textured.

20. The implant system of claim 1 wherein the tapered cavity of the fixation component is substantially textured, and wherein the textured surface of the tapered cavity interacts with an outer surface of the connector such that movement of the fixation component with respect to the spinal rod is substantially inhibited during use.

21. The implant system of claim 1 wherein an outer surface of the connector is substantially textured, and wherein the textured outer surface of the connector interacts with the tapered cavity of the fixation component such that movement of the fixation component with respect to the spinal rod is substantially inhibited during use.

22. The implant system of claim 1 wherein the tapered cavity of the fixation component is substantially textured, and wherein an outer surface of the connector is substantially textured, and wherein the textured surface of the tapered cavity interacts with the textured outer surface of the connector such that movement of the fixation component with respect to the spinal rod is substantially inhibited during use.

23. The implant system of claim 1 wherein the textured surface is prepared by a shot peening process.

24. The implant system of claim 1 wherein the textured surface is prepared by an electric discharge process.

25. The implant system of claim 1 wherein the textured surface is prepared by forming a plurality of grooves.

26. The implant system of claim 1 wherein the fixation component further comprises a fixation device, the fixation device comprising a head, and wherein a portion of the head is positioned within the cavity, and wherein the head is positioned within the cavity such that the fixation device is rotatable along a longitudinal axis of the body during use, and wherein a surface of the head is substantially textured such that the textured surface of the head interacts with an outer surface of the connector such that rotation of the fixation device is substantially inhibited during use.

27. The implant system of claim 1 wherein the connector is inhibited from moving in a direction along the longitudinal axis of the spinal rod.

28. The implant system of claim 1 wherein the connector is inhibited from moving in a direction perpendicular to the longitudinal axis of the spinal rod.

29. The implant system of claim 1 wherein the connector is inhibited from moving in a direction along the longitudinal axis of the spinal rod, and wherein the connector is inhibited from moving in a direction perpendicular to the longitudinal axis of the spinal rod.

30. The implant system of claim 1 wherein the fixation component further comprises a fixation device, the fixation device comprising a head, and wherein the body further comprises an second cavity, and wherein a portion of the head is positioned within the second cavity such that the fixation device may rotate along a longitudinal axis of the body.

31. The implant system of claim 1 further comprising a fastener configured to engage the body and the upper section of the connector, the fastener being configured to secure the connector and the fixation component together, wherein the upper section further comprises an indentation for receiving the fastener, and wherein the fastener is a clip.

32. An implant system for fixation of the human spine, comprising:

a connector comprising an upper section and a lower section, the lower section defining an opening, the upper section defining a slot communicating with the opening;

a spinal rod axially positionable through the opening during use, the spinal rod comprising a textured surface, wherein the spinal rod is fixable within the opening by a clamping force exerted by the connector during use; and a fixation component comprising a body, the body comprising a tapered cavity, the tapered cavity comprising an inner surface, a first end and a second end, wherein the tapered cavity narrows in a direction from the first end to the second end, and wherein the connector is adapted to be at least partially disposed within the tapered cavity such that the inner surface of the tapered cavity engages and exerts a compressive force onto an outer surface of the connector to maintain the spinal rod within the opening during use, and wherein the connector is moveable within the tapered cavity to cause a width of the opening to narrow;

and wherein the inner surface of the opening of the connector interacts with the textured surface of the spinal rod during use such that movement of the connector with respect to the spinal rod is substantially inhibited during use.

33. The implant system of claim 32 wherein the opening has a width that is adjustable by moving the connector within the tapered cavity.

34. The implant system of claim 32 wherein the lower section comprises a first arm having a first tip and a second arm having a second tip, the first arm and the second arm together defining the opening such that the opening is substantially U-shaped, and wherein the slot enables the first arm and the second arm to be deflected relative to one another during use, the deflection of the arms causing a change in a distance between the first tip and the second tip during use.

35. The implant system of claim 32 wherein the fixation component further comprises a bore, and further comprising a locking element configured to extend through the bore and contact the connector to inhibit movement of the connector within the tapered cavity during use.

36. The implant system of claim 32 wherein the outer surface of the lower section has a taper that complements that of the tapered cavity.

37. The implant system of claim 32 wherein the compressive force exerted against the spinal rod is selectively variable and is a function of a depth of the lower section within the tapered cavity.

38. The implant system of claim 32 wherein the fixation component further comprises a fixation device for attaching the spinal rod to a vertebra.

39. The implant system of claim 32 wherein the body comprises a substantially U-shaped yoke having an axial length, the yoke being formed between a top section of the body and a bottom section of the body, the top section of the body comprising a first edge, the bottom section of the body comprising a second edge, the first and second edges defining a width of the yoke, and wherein the first and second edges are curved such that the width of the yoke varies across the axial length of the yoke.

40. The implant system of claim 32 wherein the fixation component further comprises a fixation device and a spacer configured to fit between the connector and the fixation component during use, the fixation device comprising protrusions, the spacer offsetting the fixation device from the spinal rod and comprising teeth configured to form a complementary engagement with the protrusions to inhibit rotation of the fixation device about the spacer during use.

41. The implant system of claim 32 wherein the body further comprises a top section and a bottom section, the tapered cavity being formed in between the top section of the body and the bottom section of the body, the top section of the body and the bottom section of the body each comprising edges that are curved, and wherein the fixation component is configured to pivot about the spinal rod in a substantially vertical plane during use, and wherein the curved edges are configured to contact the spinal rod during the pivoting of the fixation component, thereby defining a range of pivotal motion of the fixation component during use.

42. The implant system of claim 32 wherein the fixation component further comprises a transverse connector for connecting the spinal rod to a neighboring spinal rod, the transverse connector comprising a reduced section and a beveled section, the reduced section having a width less than a width of the body, the beveled section being located between the body and the reduced section, and wherein the reduced section comprises a bend to shorten a lateral distance between the spinal rod and the neighboring spinal rod.

43. The implant system of claim 32 further comprising a fastener configured to engage the body and the upper section of the connector, the fastener being configured to secure the connector and the fixation component together.

44. The implant system of claim 32 wherein a portion of the upper section is threaded, and further comprising a nut configured to engage the threaded portion of the upper section of the connector, and wherein the nut is configured to cause movement of the lower section within the tapered cavity during use such that the opening exerts a compressive force against the spinal rod to maintain the spinal rod within the opening.

45. The implant system of claim 32 wherein the spinal rod is positioned within the opening during use such that a portion of the spinal rod is exposed from the lower section of the connector.

46. The implant system of claim 32, further comprising a sleeve comprising a substantially U-shaped opening, the sleeve being configured to fit substantially about the body of the fixation component during use, and wherein the sleeve comprises an interior surface that is configured to impart a force onto the spinal rod when the sleeve is downwardly translated along the body, the force causing the connector to move into the tapered cavity during use.

47. The implant system of claim 32 wherein the opening substantially surrounds a circumferential portion of the spinal rod during use.

48. The implant system of claim 32 wherein movement of the connector in a direction from the first end to the second end causes a portion of the slot to narrow such that the lower section exerts a compressive force against the spinal rod to clamp the spinal rod within the opening during use.

49. The implant system of claim 32 wherein the fixation component further comprises a fixation device, the fixation device comprising a head, and wherein a portion of the head is positioned within the cavity, and wherein the head is positioned within the cavity such that the fixation device is rotatable along a longitudinal axis of the body during use, and wherein the connector is positionable within the cavity such that rotation of the fixation device is substantially inhibited during use.

50. The implant system of claim 32 wherein an inner surface of the opening is substantially textured.

51. The implant system of claim 32 wherein the tapered cavity of the fixation component is substantially textured, and wherein the textured surface of the tapered cavity interacts with an outer surface of the connector such that movement of the fixation component with respect to the spinal rod is substantially inhibited during use.

52. The implant system of claim 32 wherein an outer surface of the connector is substantially textured, and wherein the textured outer surface of the connector interacts with the tapered cavity of the fixation component such that movement of the fixation component with respect to the spinal rod is substantially inhibited during use.

53. The implant system of claim 32 wherein the tapered cavity of the fixation component is substantially textured, and wherein an outer surface of the connector is substantially textured, and wherein the textured surface of the tapered cavity interacts with the textured outer surface of the connector such that movement of the fixation component with respect to the spinal rod is substantially inhibited during use.

54. The implant system of claim 32 wherein the textured surface is prepared by a shot peening process.

55. The implant system of claim 32 wherein the textured surface is prepared by an electric discharge process.

56. The implant system of claim 32 wherein the textured surface is prepared by forming a plurality of grooves.

57. The implant system of claim 32 wherein the fixation component further comprises a fixation device, the fixation device comprising a head, and wherein a portion of the head is positioned within the cavity, and wherein the head is positioned within the cavity such that the fixation device is rotatable along a longitudinal axis of the body during use, and wherein a surface of the head is substantially textured such that the textured surface of the head interacts with an outer surface of the connector such that rotation of the fixation device is substantially inhibited during use.

58. The implant system of claim 32 wherein the connector is inhibited from moving in a direction along the longitudinal axis of the spinal rod.

59. The implant system of claim 32 wherein the connector is inhibited from moving in a direction perpendicular to the longitudinal axis of the spinal rod.

60. The implant system of claim 32 wherein the connector is inhibited from moving in a direction along the longitudinal axis of the spinal rod, and wherein the connector is inhibited from moving in a direction perpendicular to the longitudinal axis of the spinal rod.

61. The implant system of claim 32 further comprising a fastener configured to engage the body and the upper section of the connector, the fastener being configured to secure the connector and the fixation component together, wherein the upper section further comprises an indentation for receiving the fastener, and wherein the fastener is a clip.

62. An implant system for fixation of the human spine, comprising:
a connector comprising an upper section, a lower section and a textured outer surface, the lower section defining an opening, the upper section defining a slot communicating with the opening, the opening comprising a textured inner surface;
a spinal rod axially positionable through the opening during use, the spinal rod comprising a textured surface, wherein the spinal rod is fixable within the opening by a clamping force exerted by the connector during use; and
a fixation component comprising a body, the body comprising a tapered cavity, the tapered cavity comprising a textured inner surface, a first end and a second end, wherein the tapered cavity narrows in a direction from the first end to the second end, and wherein the connector is adapted to be at least partially disposed within the tapered cavity such that the inner surface of the tapered cavity engages and exerts a compressive force onto an outer surface of the connector to maintain the spinal rod within the opening during use, and wherein the connector is moveable within the tapered cavity to cause a width of the opening to narrow;
and wherein the textured inner surface of the tapered cavity interacts with the textured surface of the outer surface of the connector during use such that movement of the fixation device with respect to the spinal rod is substantially inhibited during use;
and wherein the inner surface of the opening of the connector interacts with the textured surface of the spinal rod during use such that movement of the connector with respect to the spinal rod is substantially inhibited during use.

63. An implant system for fixation of the human spine, comprising:
a connector comprising a lower section defining an opening, the opening comprising an inner surface;
a spinal rod axially positionable through the opening during use, wherein the spinal rod is fixable within the opening by a clamping force exerted by the connector; and
a fixation component comprising a body, the body comprising a tapered cavity, the tapered cavity comprising an inner surface, a first end and a second end, wherein the tapered cavity narrows in a direction from the first end to the second end, and wherein the connector is adapted to be at least partially disposed within the tapered cavity such that the inner surface of the tapered cavity engages and exerts a compressive force onto an outer surface of the connector to maintain the spinal rod within the opening during use, and wherein the connector is moveable within the tapered cavity to cause a width of the opening to narrow;
and wherein at least one of a surface of the spinal rod and the inner surface of the connector is substantially textured such that a frictional engagement is formed between the connector and the spinal rod, and wherein the frictional engagement inhibits movement of the connector with respect to the spinal rod.

64. A method of surgically implanting a spinal fixation system comprising:
connecting a fixation component to a portion of a spine, the fixation component comprising a body, the body comprising a cavity having an inner surface;
positioning a connector within the cavity, the connector comprising a lower section, the lower section defining an opening, the opening comprising a textured surface, and
wherein the connector is positionable within the cavity such that the inner surface of the cavity engages an outer surface of the lower section;
snapping a spinal rod into the opening, the spinal rod comprising a textured surface; and
positioning the connector within the cavity to clamp the opening around the spinal rod, wherein the textured inner surface of the opening interacts with the textured surface of the spinal rod such that movement of the connector with respect to the spinal rod is substantially inhibited.

65. The method of claim 64 wherein the cavity is a tapered cavity having a first end and a second end, the tapered cavity narrowing in a direction from the first end to the second end, and wherein the connector is positioned within the cavity by moving the connector within the tapered cavity in a direction from the first end to the second end, whereby the inner surface of the tapered cavity exerts a compressive force against the lower section to deflect the lower section and cause the lower section to clamp the spinal rod within the borehole.

66. The method of claim 64 wherein the fixation component further comprises a fixation device that engages the portion of the spine, and further comprising placing a spacer between the body and the spinal rod to laterally offset the fixation device from the spinal rod.

67. The method of claim 64, further comprising clamping a second connector onto the spinal rod after the spinal rod has been attached to the spine portion, the second connector being clamped onto the spinal rod without detaching the spinal rod from the spine portion and without altering a position of any other connectors engaged to the spinal rod.

68. The method of claim 64 wherein the spinal rod comprises a circumferential portion, and wherein the lower section surrounds greater than about π radians of the circumferential portion and less than about 2π radians of the circumferential portion after the connector is positioned within the cavity.

69. The method of claim 64, further comprising applying a distraction force to the connector to change the location of the connector on the spinal rod.

70. The method of claim 64 wherein the fixation component is attached to the spine portion with a bone screw, and further comprising pivoting the bone screw about the spinal rod to form an oblique angle between the bone screw and a longitudinal axis of the spinal rod.

71. The method of claim 64, further comprising removing a connector from the spinal rod after the spinal rod has been attached to the spine portion, the connector being removed without detaching the spinal rod from the spine portion and without altering a position of any other connectors engaged to the spinal rod.

72. The method of claim 64 wherein the connector further comprises a fastening end, and further comprising attaching a fastener to the fastening end, the fastener configured to secure the connector and the fixation component together.

73. An implant system for fixation of the human spine, comprising:
- a connector comprising a receiving end forming a borehole having an open end;
- a spinal rod axially positionable through the open end into the borehole during use, the spinal rod being fixable within the borehole by a clamping force exerted by the connector; and
- a fixation component comprising a fixation device and a body, the fixation device comprising a head, the body comprising an upper cavity and a lower cavity, and wherein a portion of the head is positioned within the lower cavity such that the fixation device may rotate along a longitudinal axis of the body; and
- and wherein the connector is adapted to be at least partially disposed within the upper cavity such that an inner surface of the upper cavity engages and exerts a compressive force onto an outer surface of the receiving end to maintain the spinal rod within the borehole during use.

74. The implant system of claim 73 wherein the receiving end comprises a first arm having a first tip and a second arm having a second tip, the first arm and the second arm together forming the borehole, and wherein an opening is defined between the first tip and the second tip, and wherein the opening has a width that is adjustable by moving the connector within the cavity during use.

75. The implant system of claim 73 wherein the receiving end further comprises a first arm having a first tip and a second arm having a second tip, the first arm and the second arm together forming the borehole, and wherein the connector further comprising a slot, the slot enabling the first arm and the second arm to be deflected relative to one another during use, the deflection of the arms causing a change in a distance between the first tip and the second tip.

76. The implant system of claim 73 wherein the fixation component further comprises a bore, and further comprising a locking element configured to extend through the bore and contact the connector to inhibit movement of the connector within the cavity during use.

77. The implant system of claim 73 wherein the fixation device is configured to attach the spinal rod to a vertebra.

78. The implant system of claim 73 wherein the spinal rod comprises a circumferential portion, and wherein greater than about $\pi$ radians and less than about $2\pi$ radians of the circumferential portion is engaged by the receiving end.

79. The implant system of claim 73 wherein the spinal rod comprises a diameter, and wherein the open end has a width defined by the first tip and the second tip, and wherein the width is adjustable by moving the connector within the cavity.

80. The implant system of claim 73 wherein the fixation component further comprises a pin, and wherein the head is semi-spherical, the head defining a borehole, and wherein the pin is positionable within the borehole and the body such that the fixation device is rotatable about the pin along a longitudinal axis of the body, and wherein the pin is adapted to inhibit rotation of the fixation member along an axis perpendicular to a longitudinal axis of the body.

81. The implant system of claim 73 wherein the head comprises at least two flat edges, the flat edges configured to engage a wall separating the upper cavity from the lower cavity, and wherein the engagement of the flat edges of the head restrict rotation of the fixation device along the longitudinal axis of the body.

82. The implant system of claim 81 wherein the rotation of the fixation device in a first direction is restricted to about 30 degrees, and wherein the rotation of the fixation device in a second direction opposite the first direction is restricted to about 30 degrees.

83. The implant system of claim 73 wherein the connector further comprises a fastening end, and wherein the system further comprises a fastener configured to engage the body and the fastening end of the connector, the fastener being configured to secure the connector and the fixation component together, and wherein the fastener is configured to be removable from the connector.

84. The implant system of claim 73 wherein the inner surface of the cavity is substantially textured, and wherein the outer surface of the connector is substantially textured, and wherein an inner surface of the borehole is substantially textured, and wherein the spinal rod is substantially textured.

85. The implant system of claim 73 wherein at least one of the inner surface of the cavity, the outer surface of the connector, an inner surface of the borehole, and the spinal rod is substantially textured.

86. An implant system for fixation of the human spine, comprising:
- a connector comprising a receiving end and a fastening end, the receiving end forming a borehole, the fastening end comprising an indentation;
- a spinal rod axially positionable within the borehole such that a portion of the spinal rod is exposed from the borehole, the spinal rod being fixable within the borehole by a clamping force exerted by the connector;
- a fixation component comprising a body, the body comprising a cavity having an inner surface, and wherein the connector is adapted to be at least partially disposed within the cavity such that the inner surface of the cavity engages an outer surface of the receiving end;
- a clip adapted to engage the indentation of the connector, the clip being adapted to secure the connector and the fixation component together, and wherein the clip is adapted to be removable from the connector; and
- wherein the fixation component and the connector are joined such that a portion of the spinal rod is exposed.

87. An implant system for fixation of the human spine, comprising:
- a connector comprising a receiving end and a tab, the receiving end forming a borehole having an open end, the tab extending from the outer surface of the connector;
- a spinal rod axially positionable through the open end into the borehole during use, the spinal rod being fixable within the borehole by a clamping force exerted by the connector; and
- a fixation component comprising a body, the body comprising a cavity, the cavity comprising a channel and an inner surface; the channel configured to receive the tab;
- and wherein the connector is adapted to be at least partially disposed within the cavity such that an inner surface of the cavity engages and exerts a compressive force onto an outer surface of the receiving end to maintain the spinal rod within the borehole during use;
- and wherein the tab is configured to fit within the channel when the connector is disposed within the cavity, and wherein the tab inhibits movement of the connector out of the cavity during use.

88. The implant system of claim 87 wherein the borehole has a width that is adjustable by moving the connector within the cavity.

89. The implant system of claim 87 wherein the connector comprises a slot, and wherein the receiving end comprises a first arm having a first tip and a second arm having a second tip, the first arm and the second arm together defining the borehole, and wherein the slot enables the first arm and the second arm to be deflected relative to one another during use, the deflection of the arms causing a change in a distance between the first tip and the second tip during use.

90. The implant system of claim 87 wherein the fixation component farther comprises a bore, and further comprising a locking element configured to extend through the bore and contact the connector to inhibit movement of the connector within the cavity during use.

91. The implant system of claim 87 wherein the cavity is a tapered cavity, and wherein the outer surface of the receiving end has a taper that complements that of the tapered cavity, and wherein the receiving end is configured to be moved within the cavity such that the inner surface of the cavity exerts a compressive force against the outer surface of the receiving end to clamp the spinal rod within the opening during use.

92. The implant system of claim 87 wherein the compressive force exerted against the spinal rod is selectively variable and is a function of a depth of the receiving end within the cavity.

93. The implant system of claim 87 wherein the fixation component further comprises a fixation device for attaching the spinal rod to a vertebra.

94. The implant system of claim 87 wherein the body comprises a substantially U-shaped yoke having an axial length, the yoke being formed between a top section of the body and a bottom section of the body, the top section of the body comprising a first edge, the bottom section of the body comprising a second edge, the first and second edges defining a width of the yoke, and wherein the first and second edges are curved such that the width of the yoke varies across the axial length of the yoke.

95. The implant system of claim 87 wherein the fixation component further comprises a fixation device and a spacer configured to fit between the connector and the fixation component, the fixation device comprising protrusions, the spacer offsetting the fixation device from the spinal rod and comprising teeth configured to form a complementary engagement with the protrusions to inhibit rotation of the fixation device about the spacer during use.

96. The implant system of claim 87 wherein the body further comprises a top section and a bottom section, the cavity being formed in between the top section of the body and the bottom section of the body, the top section of the body and the bottom section of the body each comprising edges that are curved, and wherein the fixation component is configured to pivot about the spinal rod in a substantially vertical plane during use, and wherein the curved edges are configured to contact the spinal rod during the pivoting of the fixation component, thereby defining a range of pivotal motion of the fixation component during use.

97. The implant system of claim 87 wherein the fixation component further comprises a transverse connector for connecting the spinal rod to a neighboring spinal rod, the transverse connector comprising a reduced section and a beveled section, the reduced section having a width less than a width of the body, the beveled section being located between the body and the reduced section, and wherein the reduced section comprises a bend to shorten a lateral distance between the spinal rod and the neighboring spinal rod.

98. The implant system of claim 87 further comprising a fastening end, wherein a portion of the fastening end is threaded, and further comprising a nut configured to engage the threaded portion of the fastening end, and wherein the nut is configured to cause movement of the receiving end within the cavity during use such that the borehole exerts a compressive force against the spinal rod to maintain the spinal rod within the opening during use.

99. The implant system of claim 87 wherein the spinal rod is positioned within the borehole and wherein a portion of the spinal rod is exposed from the receiving end of the connector during use.

100. The implant system of claim 87, further comprising a sleeve comprising a substantially U-shaped opening, the sleeve being configured to fit substantially about the body of the fixation component during use, and wherein the sleeve comprises an interior surface that is configured to impart a force onto the spinal rod when the sleeve is downwardly translated along the body, the force causing the connector to move into the tapered cavity during use.

101. The implant system of claim 87 wherein the fixation component further comprises a fixation device, the fixation device comprising a head, and wherein a portion of the head is positioned within the cavity, and wherein the head is positioned within the cavity such that the fixation device is rotatable along a longitudinal axis of the body during use, and wherein the connector is positionable within the cavity such that rotation of the fixation device is substantially inhibited during use.

102. The implant system of claim 87 wherein the inner surface of the cavity is substantially textured, and wherein the outer surface of the connector is substantially textured, and wherein an inner surface of the borehole is substantially textured, and wherein the spinal rod is substantially textured.

* * * * *

UNITED STATES PATENT AND TRADEMARK OFFICE
CERTIFICATE OF CORRECTION

PATENT NO. : 5,989,250
DATED : November 23, 1999
INVENTOR(S) : Erik J. Wagner, Vincent J. Jannetty, Robert J. Jones It is certified that error appears in the above-identified patent and that said Letters Patent is hereby corrected as shown below:

In the Claims:

Claim 79, col. 35, line 49, please delete "Claim 73" and substitute therefor --Claim 74--.

Claim 90, col. 37, line 10, please delete "farther" and substitute --further--.

Signed and Sealed this

Twenty-first Day of November, 2000

Attest:

Q. TODD DICKINSON

*Attesting Officer*   *Director of Patents and Trademarks*